US010503150B2

(12) United States Patent
Chen et al.

(10) Patent No.: US 10,503,150 B2
(45) Date of Patent: Dec. 10, 2019

(54) METHOD FOR PRECISE LOCALIZATION AND TREATMENT OF A TARGET SITE AND A MEDICAL AUXILIARY APPARATUS

(71) Applicant: SHANGHAI PULMONARY HOSPITAL, Shanghai (CN)

(72) Inventors: Chang Chen, Shanghai (CN); Mu Li, Shanghai (CN); Lei Zhang, Shanghai (CN); Zeyao Li, Shanghai (CN); Long Wang, Shanghai (CN); Donglai Chen, Shanghai (CN); XierMaiMaiTi Kadeer, Shanghai (CN); Yawei Gu, Shanghai (CN); Ziwen Fan, Shanghai (CN)

(73) Assignee: SHANGHAI PULMONARY HOSPITAL, Shanghai (CN)

( * ) Notice: Subject to any disclaimer, the term of this patent is extended or adjusted under 35 U.S.C. 154(b) by 203 days.

(21) Appl. No.: 15/673,626

(22) Filed: Aug. 10, 2017

(65) Prior Publication Data
US 2018/0267507 A1 Sep. 20, 2018

(30) Foreign Application Priority Data

Mar. 16, 2017 (CN) .......................... 2017 1 0156054

(51) Int. Cl.
A61B 34/10 (2016.01)
G05B 19/4099 (2006.01)
A61B 17/34 (2006.01)
B33Y 80/00 (2015.01)
B29C 64/393 (2017.01)
(Continued)

(52) U.S. Cl.
CPC ...... *G05B 19/4099* (2013.01); *A61B 17/3403* (2013.01); *B29C 64/393* (2017.08); *B33Y 50/02* (2014.12); *B33Y 80/00* (2014.12); *G16H 50/50* (2018.01); *B29L 2031/753* (2013.01); *G05B 2219/35134* (2013.01); *G05B 2219/49007* (2013.01)

(58) Field of Classification Search
CPC ..... A61B 34/10; A61B 90/10; A61B 17/3403; A61B 17/17; A61B 17/1739; A61B 2017/3405; A61B 2017/3407; A61B 2034/105; A61B 2034/108; G05B 19/4099
See application file for complete search history.

(56) References Cited

U.S. PATENT DOCUMENTS 6,122,541 A * 9/2000 Cosman ................. A61B 90/10
600/426
6,327,491 B1 * 12/2001 Franklin ................. A61B 90/11
600/429
(Continued)

Primary Examiner — Christopher L Templeton
(74) Attorney, Agent, or Firm — Andrew F. Young, Esq.; Lackenbach Siegel, LLP

(57) ABSTRACT

The present invention discloses a method for precise localization and treatment of a target site, which builds a 3D digital model of an anatomical structure of a patient in accordance with tomographic image data of the patient; a structure model for locating a target site which comprises a template model for locating a target site and an angle locating auxiliary unit model is customized, and a position and an angle for loading and treating a target site are designed according to 3D position of the target site; then a target site locating structure is printed by 3D printing technology, and the target site locating structure is utilized to treat the target site.

13 Claims, 9 Drawing Sheets

(51) Int. Cl.
    *B33Y 50/02*     (2015.01)
    *G16H 50/50*     (2018.01)
    *B29L 31/00*     (2006.01)

(56) References Cited

U.S. PATENT DOCUMENTS

| | | | | |
|---|---|---|---|---|
| 9,707,049 | B1* | 7/2017 | Allen | A61B 90/11 |
| 2005/0075649 | A1* | 4/2005 | Bova | A61B 90/10 |
| | | | | 606/130 |
| 2006/0212044 | A1* | 9/2006 | Bova | A61B 90/10 |
| | | | | 606/130 |
| 2008/0171930 | A1* | 7/2008 | Abolfathi | A61B 90/11 |
| | | | | 600/410 |
| 2009/0030338 | A1* | 1/2009 | Crocker | A61B 10/025 |
| | | | | 600/562 |
| 2011/0118527 | A1* | 5/2011 | Giesel | A61N 5/1049 |
| | | | | 600/1 |
| 2013/0041381 | A1* | 2/2013 | Clair | A61B 17/171 |
| | | | | 606/96 |
| 2013/0274778 | A1* | 10/2013 | Mercier | A61B 17/1739 |
| | | | | 606/172 |
| 2014/0350572 | A1* | 11/2014 | Elhawary | A61B 90/11 |
| | | | | 606/130 |
| 2017/0135706 | A1* | 5/2017 | Frey | A61B 17/1703 |

\* cited by examiner

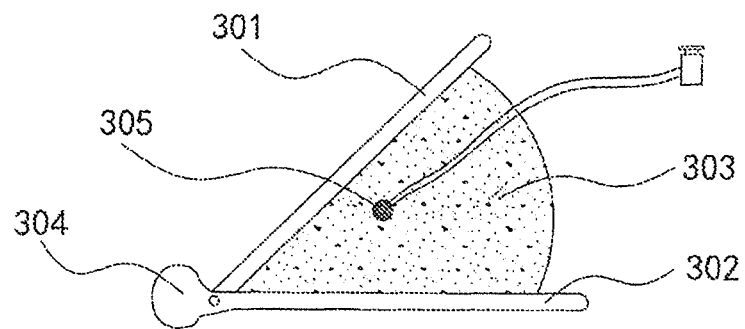
FIG. 9
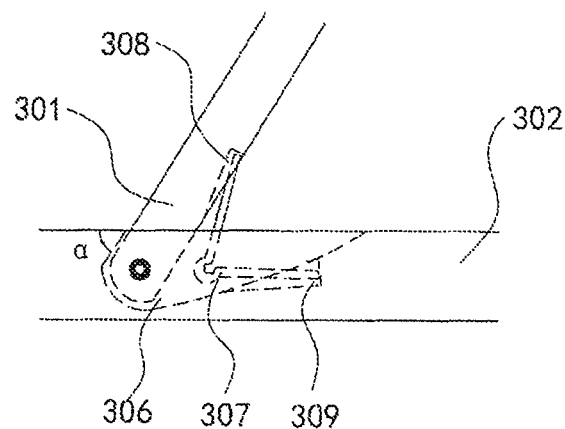
FIG. 10
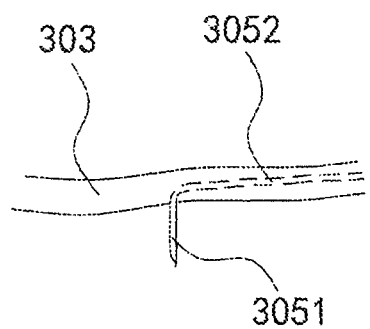
FIG. 11-a
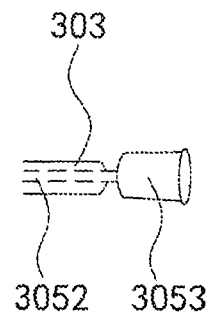
FIG. 11-b

METHOD FOR PRECISE LOCALIZATION AND TREATMENT OF A TARGET SITE AND A MEDICAL AUXILIARY APPARATUS

CROSS-REFERENCE TO RELATED APPLICATIONS

The present application claims priority to and the benefit of Chinese Patent Application No. CN 201710156054.0, filed on Mar. 16, 2017, the entire content of which is incorporated herein by reference.

BACKGROUND OF THE INVENTION

1. Field of the Invention

The present invention relates to a method for precise localization and treatment of a target site, especially to a method for precise localization and treatment of a target site in vivo and in vitro, and an extracorporeal medical auxiliary apparatus and a production method thereof based on the method for precise localization and treatment.

2. Description of the Related Art

Various pulmonary nodules including Ground-Glass Opacity (GGO) are important operation indications of thoracoscopic pulmonary surgery. If the nodule is too small and deep, it will be difficult to properly resect the nodule due co the challenge of the nodule localization. Currently, for solving this clinical problem, it is provided three main methods to locate pulmonary nodules: 1, probe locating during surgery: a touching method is used in a probable region of a pulmonary nodule for locating the pulmonary nodule based on chest CT during surgery; 2, a hook-wire locating needle through a thoracic wall for locating a pulmonary nodule under guidance of CT: a hook-wire locating needle is used to puncture a lung through a thoracic wall under guidance of CT before surgery; after repealed adjustments and attempt, the needle is gradually approaching the position of a pulmonary mass, then the "hooked" metal hook-wire is released and remained near the pulmonary mass for locating the pulmonary mass; during surgery, as long as the position of the needle of the hook-wire is found, the pulmonary mass can be assisted located so that an excision region of pulmonary tissues can be determined; 3, a micro-coil through a thoracic wall for locating a pulmonary nodule under guidance of CT before surgery: similar to the abovementioned hook-wire method, a micro-coil is used to puncture a lung through a thoracic wall for locating pulmonary nodules under guidance of CT before surgery; the major difference is that the released foreign body is a micro-coil rather than a metal hook after puncture in place; during surgery, as long as a surgeon touches the position of the micro-coil, a required excision region of pulmonary tissues can be determined.

However, the related prior art has following technical defects: a, a palpation method cannot detect a pulmonary nodule during surgery: theoretically, a palpation method is the most direct and accurate method for locating lung nodule during surgery, however, the palpation method often fails for various reasons, such as a pulmonary nodule with low density, small size, deep position and inexperienced surgeons during surgery; b, radiation influence: when a hook-wire loaning needle or a micro-coil is utilized to introduce puncture localization under guidance of CT before surgery, a patient has to be subjected to CT scan repeatedly for localization in a short term, so it is inevitable that the patient would have to receive high dose of radiation exposure; c, staffing and cost: when a hook-wire locating needle or a micro-coil is utilized to introduce puncture localization under guidance of CT scan before surgery, at least two experienced medical staffs are required to operate. On the one hand, the learning curve of training medical staffs is flat and a period of training is so long, on the other hand, the heavy workload of medical staffs, medical expense and economic burden of patients are increased.

Existing localization method before surgery usually takes a long time, and a patient is required to lie on the examining CT bed of scanner in a fixed posture for a long period, suffering from repeated adjustments and multiple punctures of a puncture needle. Especially, it is totally impracticable for the prior art to treat an unconscious patient or a patient with critical illness who cannot cooperate during treatment.

SUMMARY OF THE INVENTION

For solving the abovementioned technical problems in the prior art, the present invention provides a method for precise localization and treatment of a target site, further provides a method for precise localization and treatment of a target site in vivo and in vitro, and a 3D printed extracorporeal medical auxiliary apparatus for localization/biopsy of a pulmonary target lesion and a production method thereof, so that the localization of a target site is more precise and the treatment effect is better. The technical principle of the method for precise localization and treatment of a target site according to the invention includes: a computer-aided design software is used for building a digital model of an anatomical structure of a patient in accordance with tomographic image data of the patient; a template model for locating a target site which closely fits a body surface or an organ surface of the digital model of the anatomical structure of the patient is customized based on the digital model, and a position and an angle of an angle locating auxiliary unit model are designed according to 3D position of the target site; then a target site locating plate with an angle locating auxiliary unit is printed by 3D printing technology, and the target site locating plate with an angle locating auxiliary unit is utilized to implement a corresponding treatment on the target site of the patient. The method for localization and treatment of a target site according to the invention could be widely used in various technical fields, such as locating before surgery, puncture biopsy and radiotherapy, wherein the term "localization and treatment" is used to refer to various operations before or during surgery, such as labeling localization, puncture biopsy, puncture drainage, stereotactic puncture, targeting excision, stereotactic radiation, disposition in a fixator for a target site.

The technical solution specifically comprises:

According to the first aspect of the invention, it is provided a method for precise localization and treatment of a target site, comprising following steps:

S1: a computer-aided design software is used for building a digital model of an anatomical structure of a patient in accordance with tomographic image data of the patient, and the 3D position of the target site is determined based on the digital model of the anatomical structure;

S2: the computer-aided design software is reused to design a template model for locating a target site which closely fits a body surface or an organ surface of the digital model of the anatomical structure of the patient based on the digital model of the anatomical structure obtained in S1; subsequently, an angle locating auxiliary unit model is designed on the template model for locating a target site according to the 3D position of the target site determined in S1, wherein the angle locating auxiliary unit model comprises an auxiliary tunnel, a relative angle of which is jointly determined by the position of the target site, the position of the angle locating auxiliary unit model and the position of relevant important organ or tissue;

S3: the template model for locating a target site with the angle locating auxiliary unit model is printed by 3D printing technology, so as to produce a target site locating structure;

S4: the target site locating structure produced in S3 is mounted on a corresponding position of a body surface or an organ surface of the patient, then a treatment device is used to correspondingly treat the target site with the assistance of the angle locating auxiliary unit.

Preferably, a method for designing the template model for locating a target site in S2 comprises:

a. a localization path which passes through the target site and has the shortest distance from a body surface or an organ surface is designed on the digital model of the anatomical structure; a point on a body surface or an organ surface is set as a puncture point according to the localization path; taking a body surface mark or an organ surface mark of the patient as a reference point, an anatomical orientation point is designed on the digital model of the anatomical structure for assisting the target site locating structure in properly placing and locating;

b. in accordance with the anatomical orientation point, the localization path and the puncture point, the computer-aided design software is used to design a template model for locating a target site which closely fits a body surface or an organ surface of the digital model of the anatomical structure.

More preferably, the auxiliary tunnel of the angle locating auxiliary unit model in S2 is configured in the localization path between the target site and the puncture point, wherein the localization path having the shortest distance is configured for detouring around important blood vessels, nerves and bones in the digital model of the anatomical structure.

Preferably, according to different clinical needs, an auxiliary mechanism for matching the locating of treatment device is configured on the angle locating auxiliary unit model in S2.

More preferably, the auxiliary mechanism comprises a fixed frame, a sterilizing hole and a guide rail steel core.

Preferably, the digital model of an anatomical structure comprises digital models of head and neck, trunk, upper limb and/or lower limb having the target site.

Preferably, localization, size, depth and number of the target site are labeled and calculated on the digital model of an anatomical structure based on tomographic image data of the patient in S1.

Preferably, the treatment device is selected from a biopsy gun, a locating needle, a radiation source, an electrode patch and a blood lancet in S4.

More preferably, the locating needle is an ejection component connected to an assembled biopsy gun or an ejection component of a disposable blood taking syringe for blood glucose.

Preferably, the computer-aided design software is selected from Mimics, Magics, Geomagic Studio, 3Dmax, PROE, UG, AUTOCAD and SOLIDWORK.

According to the second aspect of the invention, it is provided a use of the method for precise localization and treatment of a target site in locating before surgery, puncture biopsy and stereotactic radiotherapy. For example, the use of the method for precise localization and treatment of a target site may include: locating pulmonary nodules before surgery, puncture biopsy for pulmonary mass, stereotactic radiotherapy for pulmonary tumor, stereotactic puncture for intracranial hematoma, deep brain stimulation, stereotactic radiotherapy for intracranial tumor, puncture biopsy for breast lumps, puncture drainage for breast abscesses, puncture drainage for heptatpostema, radiofrequency ablation for liver tumor, puncture biopsy for kidney, disposition in an orthopaedic internal fixator during surgery.

According to the third aspect of the invention, it is provided a method for precise localization and treatment of a target site in vivo, comprising following steps:

S1: a computer-aided design software is used for building a digital model of thoracic cavity/abdominal cavity and related organs of a patient in accordance with tomographic image data of the patient, and the 3D position of the target site is determined based on the digital model of thoracic cavity/abdominal cavity and related organs;

S2: the computer-aided design software is reused to design a template model for locating an intracorporal target site which closely fits an organ surface of the digital model of thoracic cavity/abdominal cavity and related organs of the patient based on the digital model of thoracic cavity/abdominal cavity and related organs obtained in S1; subsequently, an angle locating auxiliary unit model is designed on the template model for locating an intracorporal target site according to the 3D position of the target site determined in S1, wherein the angle locating auxiliary unit model comprises an auxiliary tunnel, a relative angle of which is jointly determined by the 3D position of the target site, the position of the angle locating auxiliary unit model and the position of relevant important organ or tissue;

S3: the template model for locating an intracorporal target site with the angle locating auxiliary unit model is printed by 3D printing technology, so as to produce an intracorporal target site locating structure having an auxiliary tunnel;

S4: the intracorporal target site locating structure produced in S3 is mounted on a corresponding position of an organ surface of the patient through a micro incision during surgery, then a treatment device is used to correspondingly treat the target site with the assistance of the angle locating auxiliary unit.

Preferably, a method for designing the template model for locating an intracorporal target site in S2 comprises:

a. a localization path which passes through the target site and has the shortest distance from an organ surface is designed on the digital model of thoracic, cavity/abdominal cavity and related organs; a point on an organ surface is set as a puncture point according to the localization path; taking an organ surface mark of the patient as a reference point, an anatomical orientation point is designed on the digital model of thoracic cavity/abdominal cavity and related organs for assisting the intracorporal target site locating structure in property placing and locating;

b. in accordance with the anatomical orientation point, the localization path and the puncture point, the computer-aided design software is used to design a template model for locating an intracorporal target site which closely fits an organ surface of the digital model of thoracic cavity/abdominal cavity and related organs.

Preferably, the auxiliary tunnel of the angle locating auxiliary unit model in S2 is configured in the localization path between the target site and the puncture point, wherein the localization path having the shortest distance is configured for detouring around important blood vessels, nerves and bones in the digital model of thoracic cavity/abdominal cavity and related organs.

More preferably, the organ surface mark is selected from at least two of the group of internal surface of thoracic cage, apex pulmonis, cupula of pleura, bottom of pleura, diaphragm surface, costal bone, costal joint, spine, thoracic aorta.

Preferably, localization, size, depth and number of the target site are labeled and calculated on the digital model of thoracic cavity/abdominal cavity and related organs based on tomographic image data of the patient in S1.

Preferably, the digital model of thoracic cavity/abdominal cavity and related organs comprises a plurality of digital models of the thoracic cavity, the abdominal cavity and several organs.

Preferably, the intracorporal target site locating structure is mounted on a corresponding position of an organ surface of the patient through a micro incision during surgery in case of lateral pulmonary collapse in S4; the treatment device is used to correspondingly treat the target site in case of lateral pulmonary ventilation and lung recruitment maneuvers in S4.

Preferably, the treatment device is selected from a biopsy gun, a locating needle, a radiation source, an electrode patch and a blood lancet in S4.

More preferably, the locating needle is an ejection component connected to an assembled biopsy gun or an ejection component of a disposable blood taking syringe for blood glucose.

Preferably, the computer-aided design software is selected from Mimics, Magics, Geomagic Studio, 3Dmax, PROE, UG, AUTOCAD and SOLIDWORK.

According to the fourth aspect of the invention, it is provided a method for precise localization and treatment of a target site in vitro, comprising following steps:

S1: a computer-aided design software is used for building a digital model of a body surface morphology and an anatomical bony structure of a patient in accordance with tomographic image data of the patient, and the 3D position of the target site is determined based on the digital model of the body surface morphology and the anatomical bony structure;

S2: the computer-aided design software is reused to design a template model for locating an extracorpeal target site which closely fits a body surface of the digital model of the body surface morphology and the anatomical bony structure of the patient based on the digital model of the body surface morphology and the anatomical bony structure obtained in S1; subsequently, an angle locating auxiliary unit model is designed on the template model for locating an extracorporeal target site according to the 3D position of the target site determined in S1, wherein the angle locating auxiliary unit model comprises an auxiliary tunnel, a relative angle of which is jointly determined by the position of the target site, the position of the angle locating auxiliary unit model and the position of relevant important organ or tissue;

S3: the template model for locating an extracorporeal target site with the angle locating auxiliary unit model is printed by 3D printing technology, so as to produce an extracorporeal target site locating structure having an auxiliary tunnel;

S4: the extracorporeal target site locating structure produced in S3 is mounted on a corresponding position of a body surface of the patient, then a treatment device is used to correspondingly treat the target site through a micro incision during surgery with the assistance of the angle locating auxiliary unit.

Preferably, a method for designing the template model for locating an extracorporeal target site in S2 comprises:

a. a localization path, which passes through the target sire and has the shortest distance from a body surface is designed on the digital model of the body surface morphology and the anatomical bony structure; a point on a body surface is set as a puncture point according to the localization path; taking a body surface mark of the patient as a reference point, an anatomical orientation point is designed on the digital model of the body surface morphology and the anatomical bony structure for assisting the extracorporeal target site locating structure in properly placing and locating;

b. in accordance with the anatomical orientation point, the localization path and the puncture point, the computer-aided design software is used to design a template model for locating an extracorporeal target site which closely fits a body surface of the digital model of the body surface morphology and the anatomical bony structure. More preferably, the auxiliary tunnel of the angle locating auxiliary unit model in S2 is configured in the localization path between the target site and the puncture point, wherein the localization path having the shortest distance is configured for detouring around important blood vessels, nerves and bones in the digital model of body surface morphology and the anatomical bony structure.

Preferably, the anatomical orientation point corresponds to the body surface mark of the patient, which is selected from at least two of the group of thoracic cage surface, suprasternal fossa, sternoclavicular joint, sternal angle, mesosternum, xiphoid, anterior median line, posterior median line and spinous process.

More preferably, a fixing structure for closely fitting the body surface mark is configured on a internal surface of the extracorporeal target site locating structure.

More preferably, the fixing structure is selected from at least one of the group of projection structure, depression structure, linear hollow structure and circular hollow structure.

Preferably, the treatment device is selected from a biopsy gun, a locating needle, a radiation source, an electrode patch and a blood lancet in S4.

Preferably, the locating needle is an ejection component connected to an assembled biopsy gun or an ejection component of a disposable blood taking syringe for blood glucose.

Preferably, the computer-aided design software is selected from Mimics, Magics. Geomagic Studio, 3Dmax, PROE, UG, AUTOCAD and SOLIDWORK.

According to the fifth aspect of the invention, it is provided an extracorporeal medical auxiliary apparatus for localization/biopsy of a pulmonary target lesion according to the method for precise localization and treatment of a target site in vitro, wherein the extracorporeal medical auxiliary apparatus for localization/biopsy is 3D printed and comprises:

a template for locating a pulmonary target lesion, configured to closely fit a body surface, having a triangular or butterfly structure with several raised points and/or hollow holes corresponding to body surface marks thereon; and an angle locating auxiliary unit, consisting of a guide rail for inserting needle, a guide rail receiving column and sterilizing anesthesia holes; wherein the guide rail receiving column is a cylindrical hollow structure mounted on the template for locating a pulmonary target lesion, the sterilizing anesthesia holes are set on a joint part between the guide rail receiving column and the template for locating a pulmonary target lesion, and the guide rail for inserting needle is hollow structure and detachably mounted on an upper end of the guide rail receiving column so that a puncture needle can pass through an inserting needle tunnel formed by the guide rail for inserting needle and the guide rail receiving column.

Preferably, the hollow hole comprises:

hollow wires, configured on a frame of the template for locating a pulmonary target lesion, respectively corresponding to an upper edge connecting line of a body sternoclavicular joint, an anterior median line and a posterior median line; and a circular hollow, configured on a top of the template for locating a pulmonary target lesion, corresponding to a body xiphoid;

a raised point, configured on the other top of the template for locating a pulmonary target lesion, corresponding to an upward-fovea of a body sternum.

Preferably, the angle locating auxiliary unit is mounted on a horizontal extension part of the template for locating a pulmonary target lesion.

Preferably, the sterilizing anesthesia holes are set on the side and around the bottom of the guide rail receiving column, showing semilunar open structures.

Preferably, the guide rail for inserting needle is a hollow bolt-like structure, which has a lower end configured to be inserted into a hollow cavity of the guide rail receiving column, and an upper end with a cap structure configured to prevent the guide rail for inserting needle from sliding into the hollow cavity of the guide rail receiving column. According to the sixth aspect of the invention, it is provided a production method of the 3D printed extracorporeal medical auxiliary apparatus for localization/biopsy of a pulmonary target lesion, comprising following steps:

S1: a computer-aided design software is used for building a digital model of a body surface morphology and an anatomical bony structure of a patient in accordance with pretreated CT image sequence showing a target lesion, and the 3D position of the target lesion is determined based on the digital model of the body surface morphology and the anatomical bony structure;

S2: the computer-aided design software is reused to design a template model for loaning a pulmonary target lesion which closely fits a body surface of the digital model of the body surface morphology and the anatomical bony structure of the patient based on the digital model of the body surface morphology and the anatomical bony structure obtained in S1; subsequently, an angle locating auxiliary unit model is designed on the template model for locating a pulmonary target lesion according to the 3D position of the target lesion determined in S1, wherein the angle locating auxiliary unit model comprises a guide rail receiving column, a relative angle of which is jointly determined by the position of the target lesion, the position of the angle locating auxiliary unit model and the position of relevant important organ or tissue;

S3: the template model for locating a pulmonary target lesion and the angle locating auxiliary unit model constitute a digital model of the extracorporeal medical auxiliary apparatus for localization/biopsy, wherein the digital model of the extracorporeal medical auxiliary apparatus for localization/biopsy is printed by 3D printing technology, so as to produce an extracorporeal medical auxiliary apparatus for localization/biopsy having an auxiliary tunnel.

Preferably, a method for designing the template model for locating a pulmonary target lesion comprises:

a. a localization path which passes through the target lesion and has the shortest distance from a body surface is designed on the digital model of the body surface morphology and the anatomical bony structure; a point on a body surface is set as a puncture point according to the localization path, taking a body surface mark of the patient as a reference point, an anatomical orientation point is designed on the digital model of the body surface morphology and the anatomical bony structure for assisting the extracorporeal medical auxiliary apparatus for localization/biopsy in properly placing and locating;

b. in accordance with the anatomical orientation point, the localization path and the puncture point, the computer-aided design software is used to design a template model for locating a pulmonary target lesion which closely fits a body surface of the digital model of the body surface morphology and the anatomical bony structure.

Preferably, the puncture point on a body surface is set as an entry point of the angle locating auxiliary unit model according to the localization path, a connecting line between the entry point and the target lesion is set as an entry path, a distance from the center of the target lesion to the superior border of the guide rail for inserting needle is set as an inserting needle depth.

Preferably, the auxiliary tunnel of the angle locating auxiliary unit model in S2 is configured in the localization path between the target site and the puncture point, wherein the localization path having the shortest distance is configured for detouring around important blood vessels, nerves and bones in the digital model of body surface morphology and the anatomical bony structure.

Preferably, the body surface mark of the patient is selected from at least two of the group of thoracic cage surface, an upper edge connecting line of a body sternoclavicular joint, suprasternal fossa, sternoclavicular joint, sternal angle, mesosternum, xiphoid, anterior median line, posterior median line and spinous process.

Preferably, the computer-aided design software is selected from Mimics, Magics, Geomagic Studio, 3Dmax, PROE, UG, AUTOCAD and SOLIDWORK.

Preferably, the digital model of the extracorporeal medical auxiliary apparatus for localization/biopsy is 3D printed through materials selected from one or more of ABS resin, polylactic acid, PVA and nylon.

The advantageous effects of the invention includes: the method for precise localization and treatment of a target site provided by the invention mainly utilizes a customized target site locating apparatus in accordance with tomographic image data of a patient, so as to implement precise localization and treatment of a target site. The method for localization and treatment of a target site according to the invention could be widely used in various technical fields, such as locating before surgery, puncture biopsy and stereotactic radiotherapy. Specifically, the method for localization and treatment of a target site comprises a method for precise localization and treatment of a target site in vitro and a method for precise localization and treatment of a target site in vivo in accordance with different apparatuses for locating a target site, so it is convenient for medical staffs to choose the most appropriate method for localization and treatment according to the position of the target site of the patient Additionally, the present invention further provides a 3D printed extracorporeal medical auxiliary apparatus for localization/biopsy of a pulmonary target lesion, which is customized by 3D printing technology in accordance with CT image sequence showing a target lesion and data obtained from a 3D human body scanner, thereby achieving precise localization. In conclusion, the method for precise localization and treatment of a target site provided by the invention can locate and treat nodules which cannot be detected by a palpation method, reduce CT radiation quantity of a patient and radiation injury to the patient; it increases the accuracy of puncture and reduces operation time, significantly relieving the pain of the patient, it is also convenient for the patient to coordinate with treatment; it further reduces the training time of medical staffs, so the medical resource could be utilized more efficiently.

BRIEF DESCRIPTIONS OF THE DRAWINGS

FIG. 9 is a structure diagram of a V-type locating structure with film used in endoscopic surgery according to a preferred embodiment of the invention.

FIG. 10 is a partial enlarged diagram of a V-type locating structure with film used in endoscopic surgery according to a preferred embodiment of the invention.

DETAILED DESCRIPTIONS

Figure 1:
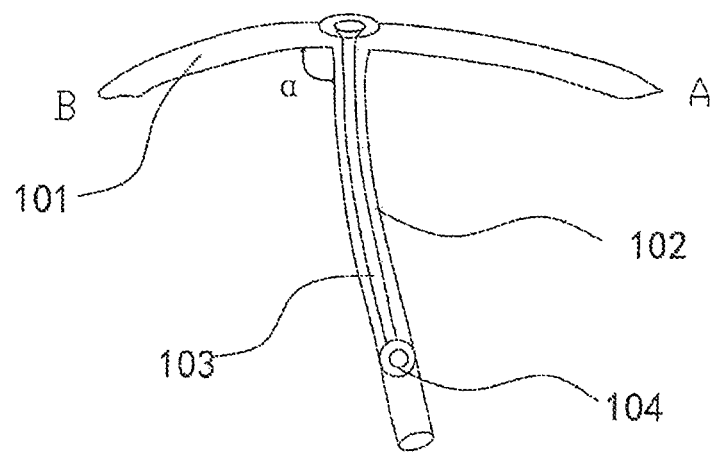
FIG. 1 is a structure diagram of a T-type locating structure within a thoracic cavity used in endoscopic surgery according to a preferred embodiment of the invention.

The embodiments with drawings shown here represent only examples of the present invention and may therefore not be understood to be limiting. Alternative embodiments that can be contemplated by the person skilled in the art are likewise included in the scope of the present invention.

The main technical solution provided by the invention is a method for precise localization and treatment of a target site, it uses a computer-aided design software to build a digital model of an anatomical structure of a patient in accordance with tomographic image data of the patient; a target site locating structure model comprising a template model for locating a target site and an angle locating auxiliary unit model is customized based on the digital model, wherein the target site locating structure model closely fits a body surface or an organ surface of the patient; a position and an angle of localization and treatment of the target site are customized according to 3D position of the target site; then the target site locating structure is printed by 3D printing technology, and the target site locating structure is utilized to implement a corresponding treatment on the target site of the patient, such as labeling and locating before surgery, puncture biopsy and other operations during surgery.

As described herein, the term "target site" refers to a patient's lesion, a target, lesion, a pulmonary mass, a pulmonary nodule or Ground-Glass Opacity (GGO) and so on, and a position of a healthy intracorporal tissue or a specific intracorporal tissue; for example, if a stereotactic radiotherapy is required to be implemented in a specific position of a patient's body, radioactive material needs to be placed in the specific position through the method for localization and treatment according to the invention. The method for precise localization and treatment of a target site according to the invention comprises following steps.

S1: a computer-aided design software is used for building a digital model of an anatomical structure of a patient in accordance with pretreated tomographic image data of the patient, and the 3D position of the target, site is determined based on the digital model of the anatomical structure;

S2: the computer-aided design software is reused to design a template model for locating a target site which closely fits a body surface or an organ surface of the digital model of the anatomical structure of the patient based on the digital model of the anatomical structure obtained in S1; subsequently, an angle locating auxiliary unit model is designed on the template model for locating a target site according to the 3D position of the target site determined in S1, wherein the angle locating auxiliary unit model comprises an auxiliary tunnel, a relative angle of which is jointly determined by the position of the target site, the position of the angle locating auxiliary unit model and the position of relevant important organ or tissue;

S3: the template model for locating a target site with the angle locating auxiliary unit model is printed by 3D printing technology, so as to produce a target site locating structure;

S4: the target site locating structure produced in S3 is mounted on a corresponding position of a body surface or an organ surface of the patient, then a treatment device is used to correspondingly treat the target site with the assistance of the angle locating auxiliary unit.

In a preferred embodiment, a method for designing the template model for locating a target site in S2 comprises:

a. a localization path which passes through the target site and has the shortest distance from a body surface or an organ surface is designed on the digital model of the anatomical structure; a point on a body surface or an organ surface is set as a puncture point according to the localization path; taking a body surface mark or art organ surface mark of the patient as a reference point, an anatomical orientation point is designed on the digital model of the anatomical structure for assisting the target site locating structure in properly placing and locating;

b. in accordance with the anatomical orientation point, the localization path and the puncture point, a graphic outline of a template for locating a target site is depicted on the surface of the digital model of the anatomical structure, wherein two sorts of graphic outline depiction exist, the first one is depicting on a body surface of the digital model of the anatomical structure when a target site is required to be located and treated in vitro, the second one is depicting on an organ surface or a body cavity surface within the digital model of the anatomical structure when a target site is required to be located and treated in vivo;

c. the computer-aided design software is used to design a template model for locating a target site which closely fits a surface of the digital model of the anatomical structure based on the depicted graphic outline.

In a preferred embodiment, the auxiliary tunnel of the angle locating auxiliary unit model in S2 is configured in the localization path between the target site and the puncture point, wherein the localization path having the shortest distance is configured for detouring around important blood vessels, nerves and bones in the digital model of the anatomical structure. Specifically, the localization path could be any straight line or any curved line so long as it detours around important blood vessels, nerves and bones and so on. Furthermore, a labeling and treating tunnel comprising the auxiliary tunnel is formed in the localization path, thus the treatment device may locate and treat precisely on the target site through the labeling and treating tunnel.

In a more preferred embodiment, an auxiliary mechanism for matching the locating of treatment device is configured on the angle locating auxiliary unit model in S2 according to different clinical requirements. The auxiliary mechanism comprises a fixed frame, a sterilizing hole and a guide rail steel core. In an exemplary embodiment, a fixed frame could be used to limit displacement of the treatment device in a certain angle during surgery, so that the treatment device could locate and treat precisely on the target site. In an exemplary embodiment, a sterilizing hole which is set near the auxiliary tunnel is used for sterilizing operation on a body surface or an organ surface of a patient, so after the target site locating structure is mounted on a corresponding position of a body surface or an organ surface of the patient, local anesthesia is operated through the sterilizing hole, and then the treatment device passes through sterilized body surface or organ surface of the patient along the auxiliary tunnel in a certain angle and reaches a part near the target site accurately, then it is used to correspondingly treat the target site with the assistance of the angle locating auxiliary unit during surgery. In an exemplary embodiment, a guide rail steel core could be used to transfer the treatment device to a pan near the target site through the labeling and treating tunnel comprising the auxiliary tunnel, then the treatment device could be controlled to treat the target site in vitro.

In a preferred embodiment, the digital model of an anatomical structure comprises digital models of head and neck, chest, abdomen, upper limb and/or lower limb containing the target site. Location, size, depth and number of the target site are labeled and calculated on the digital model of an anatomical structure before building up the digital model of an anatomical structure based on tomographic image data of the patient in S1.

In a preferred embodiment, the treatment device is selected from a biopsy gun, a locating needle, a radiation source, an electrode patch and a blood lancet in S4. In a more preferred embodiment, the locating needle is an ejection component connected to an assembled biopsy gun or an ejection component of a disposable blood taking syringe for blood glucose.

In a preferred embodiment, the computer-aided design software is selected from Mimics, Magics, Geomagic Studio, 3Dmax, PROE, UG, AUTOCAD and SOLIDWORK or other software which could build up a digital model of an anatomical structure of a patient in accordance with tomographic image data of the patient.

The method for localization and treatment of a target site according to the invention could be widely used in various technical fields, such as locating before surgery, puncture biopsy and stereotactic radiotherapy. For example, the use of the method for precise localization and treatment of a target site may include: locating pulmonary nodules before surgery, puncture biopsy for pulmonary mass, stereotactic radiotherapy for pulmonary tumor, stereotactic puncture for intracranial hematoma, deep brain stimulation, stereotactic radiotherapy for intracranial tumor, puncture biopsy for breast lumps, puncture drainage for breast abscesses, puncture drainage for hepatapostema, radiofrequency ablation for liver tumor, puncture biopsy for kidney, disposition in an orthopaedic internal fixator during surgery.

Based on different operating position of a target site, the technical solution of a method for localization and treatment of a target site includes a method for precise localization and treatment of a target site in vivo and a method for precise localization and treatment of a target site in vitro. As a result, medical staffs may choose the most appropriate method for localization and treatment of a target site according to the specific position of a target site of a patient. Taking localization and treatment of a pulmonary target lesion for example, there is a method for precise localization and treatment of a pulmonary target lesion in vivo and a method for precise localization and treatment of a pulmonary target lesion in vitro; relatively speaking, it is more accurate to use a method for precise localization and treatment in vitro than a method for precise localization and treatment in vivo for locating and treating a pulmonary target lesion of a patient.

A method for precise localization and treatment of a target site in vivo is provided, comprising following steps:

S1: a computer-aided design software is used for building up a digital model of thoracic cavity/abdominal cavity and related organs of a patient in accordance with pretreated CT image sequence showing a target site, and the 3D position of the target site is determined based on the digital model of thoracic cavity/abdominal cavity and related organs;

S2: the computer-aided design software is reused to design a template model for locating an intracorporal target, site which closely fits a thoracic cavity/abdominal cavity surface or an organ surface of the digital model of thoracic cavity/abdominal cavity and related organs of the patient based on the digital model of thoracic cavity/abdominal cavity and related organs obtained in S1; subsequently, an angle locating auxiliary unit model is designed on the template model for locating an intracorporal target site according to the 3D position of the target site determined in S1, wherein the angle locating auxiliary unit model comprises an auxiliary tunnel, a relative angle of which is jointly determined by the 3D position of the target site, the position of the angle locating auxiliary unit model and the position of relevant important organ or tissue;

S3: the template model for locating an intracorporal target site with the angle locating auxiliary unit model is printed by 3D printing technology, so as to produce art intracorporal target site locating structure having an auxiliary tunnel;

S4: the intracorporal target site locating structure produced in S3 is mounted on a corresponding position of a thoracic cavity surface or an organ surface of the patient through a micro incision during surgery, then a treatment device is used to correspondingly treat the target site with the assistance of the angle locating auxiliary unit.

In a preferred embodiment, a method for designing the template model for locating an intracorporal target site in S2 comprises:

a. a localization path which passes through the target site and has the shortest distance from a thoracic cavity surface or an organ surface is designed on the digital model of thoracic cavity/abdominal cavity and related organs; a point on an organ surface is set as a puncture point according to the localization path; taking a thoracic cavity surface mark or an organ surface mark of the patient as a reference point, an anatomical orientation point is designed on the digital model of thoracic cavity/abdominal cavity and related organs for assisting the intracorporal target site locating structure in properly placing and locating;

b. in accordance with the anatomical orientation point, the localization path and the puncture point, a graphic outline of a template for locating an intracorporal target site is depicted on the organ surface of the digital model of thoracic cavity/abdominal cavity and related organs;

c. the computer-aided design software is used to design a template model for locating an intracorporal target site which closely fits a surface of the digital model of thoracic cavity/abdominal cavity and related organs based on the depicted graphic outline.

In a more preferred embodiment, the auxiliary tunnel of the angle locating auxiliary unit model in S2 is configured in the localization path between the target site and the puncture point, wherein the localization path having the shortest distance is configured for detouring around important blood vessels, nerves and bones in the digital model of thoracic cavity/abdominal cavity and related organs. Specifically, the localization path could be any straight line or any curved line so long as it detours around important blood vessels, nerves and bones and so on. Furthermore, a labeling and treating tunnel comprising the auxiliary tunnel is formed in the localization path, thus the treatment device may implement precise localization and treatment on the intracorporal target sue through the labeling and treating tunnel.

In a more preferred embodiment, the thoracic cavity surface mark or the organ surface mark is selected from at least two of the group of an upper edge connecting line of a body sternoclavicular joint internal surface of thoracic cage, apex pulmonis, cupula of pleura, bottom of pleura, diaphragm surface, costal bone, costal joint, spine, thoracic aorta.

In a preferred embodiment, localization, size, depth and number of the target site are labeled and calculated on the digital model of thoracic cavity/abdominal cavity and related organs based on tomographic image data of the patient in S1.

In a preferred embodiment, the digital model of thoracic cavity/abdominal cavity and related organs comprises a plurality of digital models of the thoracic cavity, the abdominal cavity and several organs.

In a preferred embodiment, the intracorporal target site locating structure is mounted on a corresponding position of an organ surface within the thoracic cavity of the patient through a micro incision during surgery in ease of lateral pulmonary collapse in S4; the treatment device is used to correspondingly treat the target site in case of lateral pulmonary ventilation and lung recruitment maneuvers in S4.

In a preferred embodiment, the treatment device is selected from a biopsy gun, a locating needle, a radiation source, an electrode patch and a blood lancet in S4. In a more preferred embodiment, the locating needle is an ejection component connected to an assembled biopsy gun or an ejection component of a disposable blood taking syringe for blood glucose.

In a preferred embodiment, the computer-aided design software is selected from Mimics, Magics, Geomagic Studio, 3Dmax, PROE, UG, AUTOCAD and SOLIDWORK or other software which could build a digital model of thoracic cavity/abdominal cavity and related organs of a patient in accordance with tomographic image data of the patient.

A method for precise localization and treatment of a target site in vitro is provided, comprising following steps:

S1: a computer-aided design software is used for building a digital model of a body surface morphology and an anatomical bony structure of a patient in accordance with pretreated CT image sequence showing a target site, and the 3D position of the target site is determined based on the digital model of the body surface morphology and the anatomical bony structure;

S2: the computer-aided design software is reused to design a template model for locating an extracorporeal target site which closely fits a body surface of the digital model of the body surface morphology and the anatomical bony structure of the patient based on the digital model of the body surface morphology and the anatomical bony structure obtained in S1; subsequently, an angle locating auxiliary unit model is designed on the template model for locating an extracorporeal target site according to the 3D position of the target site determined in S1, wherein the angle locating auxiliary unit model comprises an auxiliary tunnel, a relative angle of which is jointly determined by the position of the target site, the position of the angle locating auxiliary unit model and the position of relevant important organ or tissue;

S3: the template model for locating an extracorporeal target site with the angle locating auxiliary unit model is printed by 3D printing technology, so as to produce an extracorporeal target site locating structure having an auxiliary tunnel;

S4: the extracorporeal target site locating structure produced in S3 is mounted on a corresponding position of a body surface of the patient, then a treatment device is used to correspondingly treat the target site through a micro incision during surgery with the assistance of the angle locating auxiliary unit.

In a preferred embodiment, a method for designing the template model for locating an extracorporeal target site in S2 comprises:

a. a localization path which passes through the target site and has the shortest distance from a body surface is designed on the digital model of the body surface morphology and the anatomical bony structure; a point on a body surface is set as a puncture point according to the localization path; taking a body surface mark of the patient as a reference point, an anatomical orientation point is designed on the digital model of the body surface morphology and the anatomical bony structure for assisting the extracorporeal target site locating structure in properly placing and locating;

b. in accordance with the anatomical orientation point, the localization path and the puncture point, a graphic outline of a template for locating an extracorporeal target site is depicted on the body surface of the digital model of the body surface morphology and the anatomical bony structure;

c. the computer-aided design software is used to design a template model for locating an extracorporeal target site which closely fits a surface of the digital model of the body surface morphology and the anatomical bony structure based on the depicted graphic outline.

In a more preferred embodiment, the auxiliary tunnel of the angle locating auxiliary unit model in S2 is configured in the localization path between the target site and the puncture point, wherein the localization path having the shortest distance is configured for detouring around important blood vessels, nerves and bones in the digital model of body surface morphology and the anatomical bony structure.

Specifically, the localization path could be any straight line or any curved line so long as it detours around important blood vessels, nerves and bones and so on. Furthermore, a labeling and treating tunnel comprising the auxiliary tunnel is formed in the localization path, thus the treatment device may implement precise localization and treatment on the target site through the labeling and treating tunnel.

In a preferred embodiment, the anatomical orientation point corresponds to the body surface mark of the patient, which is selected from at least two of the group of thoracic cage surface, suprasternal fossa, sternoclavicular joint, sternal angle, mesosternum, xiphoid, anterior median line, posterior median line and spinous process.

In a more preferred embodiment, a fixing structure far closely fitting the body surface mark is configured on the anatomical orientation point, wherein the fixing structure is selected from at least one of the group of projection structure, depression structure, linear hollow structure and circular hollow structure.

In a preferred embodiment the treatment device is selected from a biopsy gun, a locating needle, a radiation source, an electrode patch and a blood lancet in S4. In a more preferred embodiment, the locating needle is an ejection component connected to an assembled biopsy gun or an ejection component of a disposable blood taking syringe for blood glucose.

In a preferred embodiment, the computer-aided design software is selected from Mimics, Magics, Geomagic Studio, 3DMax, PROE, UG, AUTOCAD and SOLIDWORK or other software which could build a digital model of a body surface morphology and an anatomical bony structure of a patient in accordance with tomographic image data of the patient.

In conclusion, the method for precise localization and treatment of a target site provided by the present invention comprises a method far precise localization and treatment of a target site in vivo and a method for precise localization and treatment of a target site in vitro in accordance with different operation place of a target site. More specifically, according to different positions of target sites in combination with corresponding intracorporal thoracic cavity surface or organ surface or other tissue surface, we can know that a plurality of intracorporal target site locating and treating structures, such as a T-type locating structure, an L-type locating structure, a V-type locating structure with film within a thoracic cavity, or other intracorporal locating and treating structures specific to pulmonary mass and/or Ground-Glass Opacity (GGO) of a patient, could be derived from the method for precise localization and treatment of a target site in vivo; likewise, a plurality of extracorporeal target site locating and treating structures, such as an extracorporeal medical auxiliary apparatus for localization/biopsy of an octopus structure or a triangular structure or a butterfly structure, or other extracorporeal locating and treating structures specific to pulmonary mass and/or GGO of a patient, could be derived from the method for precise localization and treatment of a target site in vitro; both of the above fail Into the protection scope of the invention.

The embodiments set forth below represent the information to enable those skilled in the an to practice the embodiments and illustrate preferred mode of practicing the embodiments. Upon reading the following description in light of the accompanying drawing figures, those skilled in the art will understand the concepts of the disclosure and will recognize applications of these concepts not particularly addressed herein. It should be understood that these concepts and applications also fall within the scope of the disclosure and the appended claims.

Example 1

This example provides a T-type locating method within a thoracic cavity used in endoscopic surgery for GGO, comprising following steps:

S1: tomographic image data of a chest of a patient is obtained by CT scanning the chest of the patient, a computer-aided design software is used for building a digital model of the thoracic cavity and the lung with pulmonary mass of the patient, and the 3D position of the GGO is determined based on the digital model of the thoracic cavity and the lung with pulmonary mass;

S2: the computer-aided design software is reused to customized design a T-type locating structure model for locating GGO which closely fits a thoracic cavity surface of the digital model of the thoracic cavity and the lung with pulmonary mass based on the digital model of file thoracic cavity and the lung with pulmonary mass obtained in S1; subsequently, an angle locating auxiliary unit model is designed on the T-type locating structure model for locating GGO according to the 3D position of the GGO determined in S1, wherein the angle locating auxiliary unit model comprises an auxiliary tunnel, a relative angle of which is jointly determined by the position of the GGO, the position of the angle locating auxiliary unit model and the position of relevant important organ or tissue;

S3: the T-type locating structure having the auxiliary tunnel and corresponding to characteristics of the thoracic cavity of the patient is printed by 3D printing technology and based on 3D reconstructed images, wherein the T-type locating structure has a vertical portion, on which a treatment device is mounted; the treatment device is particularly located based on a locating piece image;

S4: the T-type locating structure is conformally imbedded into a thoracic cavity of the patient, and an upper surface of a horizontal portion fits the thorax around a micro incision and one end of the horizontal portion points to the suprasternal fossa, so as to secure the T-type locating structure in the thoracic cavity, then a treatment device is used to label a pleural surface with GGO.

In this example, the T-type locating structure is an intracorporal pulmonary target lesion locating structure according to the invention; the horizontal portion of the T-type locating structure is a template for locating a target site according to the invention, and the vertical portion of the T-type locating structure is an angle locating auxiliary unit according to the invention.

In this example, CT scanning in S1 is implemented for labelling and calculating localization, size, depth and number of the GGO within the lung of the patient. A method for designing the T-type locating structure model in S2 comprises:

a. a localization path which passes through the pulmonary mass and has the shortest distance from a thoracic cavity surface or an organ surface is designed oil the digital model of the thoracic cavity and the lung with pulmonary mass; a point on an organ surface is set as a puncture point according to the localization path, wherein a position of a puncture point is set according to a position of a micro incision; taking a thoracic cavity surface mark or an organ surface mark of the patient as a reference point, an anatomical orientation point is designed on the digital model of the thoracic cavity and the lung with pulmonary mass for assisting the intracorporal target site locating structure in properly placing and locating; additionally, the anatomical orientation point corresponds to a thoracic cage surface or a suprasternal fossa around a micro incision of the patient;

b. in accordance with the anatomical orientation point; the localization path and the puncture point, a graphic outline of T-type locating structure model is depicted on the organ surface of the digital model of the thoracic cavity and the lung with pulmonary mass;

c. the computer-aided design software is used to design the T-type locating structure model which closely fits a surface of the digital model of the thoracic cavity and the lung with pulmonary mass based on the depicted graphic outline.

The auxiliary tunnel of the vertical portion in S2 is configured in the localization path between the pulmonary mass and the puncture point, wherein the localization path having the shortest distance is configured for detouring around important blood vessels, nerves and bones in the digital model of the thoracic cavity and the lung with pulmonary mass under the instruction of a surgeon. Furthermore, conformally imbedding the T-type locating structure into a thoracic cavity of the patient in S4 is carried out in case of lateral pulmonary collapse; labelling anti locating a pleural surface with GGO is carried out in case of lateral pulmonary ventilation and lung recruitment maneuvers, and the treatment device is located by a color marker or an electric burning marker.

As shown in FIG. 1, in this example, the T-type locating structure is a 3D printed structure in "T" shape, and it comprises a horizontal portion 101 and a vertical portion 102. A top of the vertical portion 102 is connected to a middle part of the horizontal portion 101 at an angle α, a hollow tube 103 which is communicated with the surface of the horizontal portion 101 is configured within the vertical portion 102, the lower end of the vertical portion 102 is sealed, and a treatment device which is connected with the hollow tube 103 is configured on the vertical portion 102. In use, the T-type locating structure is conformally imbedded into a thoracic cavity of the patient and fixed, and the treatment device is utilized to label a position of GGO.

Figures 2, 3:
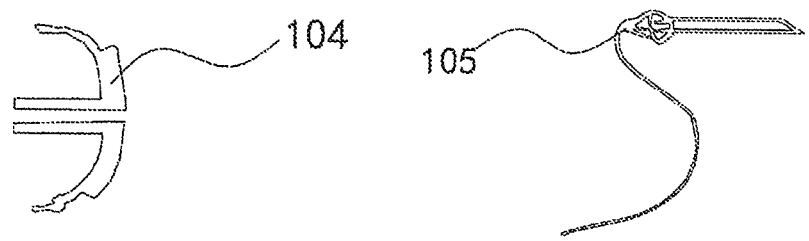
FIG. 2 is a sectional view of a vertical portion of a T-type locating structure within a thoracic cavity used in endoscopic surgery according to a preferred embodiment of the invention, showing a locating point on the vertical portion.
FIG. 3 is a structure diagram of a locating needle of a T-type locating structure within a thoracic cavity used in endoscopic surgery according to a preferred embodiment of the invention.

Specifically, the T-type locating structure provided by this example is a structure in "T" shape, comprising a horizontal portion 101 and a vertical portion 102, wherein a cylindrical hollow tube 103 is configured within the vertical portion 102, with an external diameter of 1-3 cm and an internal diameter of 0.5 cm and a length designed in accordance with 3D reconstruction model of a thoracic cavity of a patient, a position of GGO and a position of a micro surgical incision. A top of the vertical portion 102 is connected to a middle part of the horizontal portion 101 at an angle α, which is determined by 3D reconstruction model of a thoracic cavity of a patient, a position of GGO and a position of a micro surgical incision. A treatment device may be produced on a locating point 104 on the vertical portion 102 according to the position of GGO of the patient. As shown in FIG. 2, the treatment device is connected with the hollow tube 103 of the vertical portion 102, the treatment device may be a locating needle 105, as shown in FIG. 3, the locating needle 105 has an external diameter of 0.5 mm, an internal diameter of 0.4-0.45 mm and a length of 1.5-2 cm. A medical color developing agent is added into a hollow tube of the locating needle 105, after reaching the desired position, dyeing locating is completed by inserting the locating needle 105 into a visceral pleura corresponding to projected GGO. The locating needle 105 may be designed as an ejection component connected to an assembled biopsy gun or an ejection component of a disposable blood taking syringe for blood glucose, wherein a trigger could be used to control a needle ejector system for the locating needle piercing through the GGO. The treatment device may be an electrode patch, and the hollow tube of the T-type locating structure may be filled with batteries or wires, after reaching the desired position, labelling and locating is completed by activating current on a visceral pleura corresponding to projected GGO for electric burning.

Figure 4:
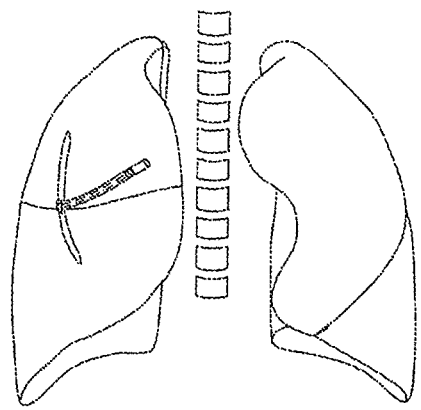
FIG. 4 is a use state diagram of a T-type locating structure within a thoracic cavity used in endoscopic surgery according to a preferred embodiment of the invention.

In this example, the upper surface of the horizontal portion 101 of the T-type locating structure is a curved surface, the middle part of the horizontal portion 101 which is connected to the top of the vertical portion 102 has a hole on its surface, wherein the hole is an aperture of the hollow tube 103 within the vertical portion 102. The specific shape of the curved surface is designed in accordance with 3D reconstruction model of thoracic cage surface around a micro incision while a patient filling his/her lung with air in horizontal position. As shown in FIG. 1 and FIG. 4, the horizontal portion 101 has an end A and an end B, wherein the end A is directed to suprasternal fossa while locating.

In this example, a method for producing the T-type locating structure comprises following steps:

S1: a computer-aided design software is used for building a digital model of the thoracic cavity and the lung with pulmonary mass of the patient in accordance with a pretreated locating piece image showing a pulmonary mass, and the position of the GGO is determined based on the digital model of the thoracic cavity and the lung with pulmonary mass;

S2: the computer-aided design software is reused to design a fitting T-type locating structure model comprising a horizontal portion and a vertical portion based on the digital model of the thoracic cavity and the lung with pulmonary mass, according to the pretreated micro incision;

S3: the T-type locating structure model is imported into a 3D printer and 3D printed, then a treatment device which is communicated with the hollow tube is mounted on a specific position of the printed vertical portion, so that the T-type locating structure is produced, wherein the treatment device is a locating needle or an electrode patch.

In the method, the computer-aided design software is selected from Mimics, Magics, Geomagic Studio, 3Dmax, PROE, UG, AUTOCAD and SOLIDWORK. A locating piece image in S1 includes localization, size, depth and number of GGO. In S3, an angle α between 3D printed vertical portion and horizontal portion is determined by GGO on the digital model and a position of a micro incision during surgery. In S3, the position of the treatment device on the vertical portion is determined by the position of GGO on the vertical portion in the digital model. Print materials could be selected from ABS, PLA, PVA and Nylon.

When there is a need for using the T-type locating structure in this example to locate GGO in a thoracic cavity, localization, size, depth and number of the GGO of a patient are labeled and calculated through CT scanning chest of a patient before surgery; based on the chest CT data, a software supporting 3D printing technology is used for building a digital model of the thoracic cavity and the lung with GGO of the patient, the GGO is located based on the digital model, and the above mentioned T-type locating structure is designed according to the 3D reconstruction model; during surgery, the postanesthetic patient is subjected to lateral pulmonary collapse in case of one lung ventilation, the vertical portion of the T-type locating structure is imbedded into the thoracic cavity through a micro incision, and the end A of the horizontal portion fitting thoracic cage surface is directed to suprasternal fossa, a chief anesthetist implements lateral pulmonary ventilation and lung recruitment maneuvers, the vertical portion of the T-type locating structure could be used to locate a specific position and label the visceral pleura, then the position of the pulmonary nodule could be determined for endoscopic wedge resection of the lung based on the visceral pleura marker.

Application Example 1

Clinical Application of the T-Type Locating Method within a Thoracic Cavity Used in Endoscopic Surgery According to Example 1

A male patient, aged 60, with a height of 172 cm and a weight of 63 kg, was physically examined, a ground-glass nodule 0.5*0.5 cm was found in a position 1.5 cm under a horizontal fissure of a lateral segment of a middle lobe of right lung and approximately horizontally aligning to the sixth thoracic vertebra through chest CT; followed up after 2 weeks in anti-inflammatory therapy, CT reexamination showed that the ground-glass nodule expanded to 1*1 cm rather than shrinked, so doctors decided to undergo thoracoscopic surgery, wherein a surgical incision was located at an intersection point of the fourth intercostal space on the right and the anterior axillary line. Based on the chest CT images, 3Dmax was used for building a digital model of the thoracic cavity and the lung with GGO of the patient, the GGO was located based on the digital model, the straight-line distance between the GGO and the surgical incision was about 7 cm; the T-type locating structure is designed according to the 3D reconstruction model, and 3D printing technology was utilized to produce the T-type locating structure made from PLA. The vertical portion is a cylindrical hollow tube with an external diameter of 1-3 cm, an internal diameter of 0.5 cm and a length of 9 cm, and it had a locating point configured at a position 2 cm from the end thereof. After the horizontal portion fitted the thoracic cage surface and the end A was directed to suprasternal fossa, the locating point of the vertical portion was directed to the position of the GGO. A locating needle was configured on the locating point, with an external diameter of 0.5 mm and an internal diameter of 0.4 mm; a rubber pipe was connected to the locating needle, filled with methylene blue dye, having a length of 0.6 m, wherein one end of the rubber pipe that was connected to the locating needle could pass through the hollow tube of the T-type locating structure; before the T-type locating structure was fixed, the locating needle could be placed within the tube cavity of the horizontal portion. The upper surface of the horizontal portion of the T-type locating structure was a curved surface, with a length of 15 cm and a width of 4.5 cm, wherein the specific shape of the curved surface was designed in accordance with 3D reconstruction model of thoracic cage surface around a micro incision while a patient filling his/her lung with air in horizontal position, and the specific shape of the curved surface could conformally fit the thoracic cage surface of the patient.

Steps of using the T-type locating structure to locate GGO in a thoracic cavity of the patient include: the postanesthetic patient was subjected to one side lung ventilation in horizontal position, a 3 cm surgical incision was formed by a scalpel at a position between the fourth and fifth ribs of the right lung of the patient, laparoscopic apparatuses were utilized to form a surgery channel. After lateral pulmonary collapse implemented by a chief anesthetist, a rubber pipe connected with a locating needle and filled with methylene blue dye was put into a hole at the middle part of the horizontal portion of the T-type locating structure, subsequently, the vertical portion of the T-type locating structure was inserted into the thoracic cavity through the surgical incision, and the tail end of the rubber pipe hung outside of the chest incision. The horizontal portion of the T-type locating structure was fitted on the thoracic cage surface closely, while the "end A" of the horizontal portion was directed to suprasternal fossa, a chief anesthetist implemented to fill the lung with air and lung recruitment maneuvers to the size of the 3D reconstruction model, the position where the locating point on the vertical portion fitted the pleura of the lung surface was the target lesion marked point; finally, the rubber pipe hung outside was pushed into the thoracic cavity quickly, and the locating needle at the other end pierced out, then it pierced through the lung surface for filling dye, and the rubber pipe was taken back, a chief anesthetist implemented lateral pulmonary collapse and used endoscopic surgery instruments to take the T-type locating structure out of the incision, a localization process was done.

Example 2

This example provides an L-type locating method within a thoracic cavity used in endoscopic surgery for GGO, comprising following steps:

S1: tomographic image data of a patient chest is obtained by CT scanning, a computer-aided design software is used for building a digital model of the thoracic cavity and the lung with pulmonary mass of the patient, and the 3D position of the GGO is determined based on the digital model of the thoracic cavity and the lung with pulmonary mass;

S2: the computer-aided design software is reused to customized design an L-type locating structure model for locating GGO which closely fits a thoracic cavity surface of the digital model of the thoracic cavity and the lung with pulmonary mass based on the digital model of the thoracic cavity and the lung with pulmonary mass obtained in S1; subsequently, an angle locating auxiliary unit model is designed on the L-type locating structure model for locating GGO according to the 3D position of the GGO determined in S1, wherein the angle locating auxiliary unit model comprises an auxiliary tunnel, a relative angle of which is jointly determined by the position of the GGO, the position of the angle locating auxiliary unit model and the position of relevant important organ or tissue;

S3: the L-type locating structure corresponding to characteristics of the thoracic cavity of the patient is printed by 3D printing technology and based on 3D reconstructed images, wherein a treatment device which is located based on a locating piece image is mounted on the L-type locating structure;

S4: the L-type locating structure is conformally imbedded into a thoracic cavity of the patient, the treatment device is used to label a pleural surface with GGO.

In this example, the L-type locating structure is an intracorporal pulmonary target lesion locating structure according to the invention; a vertical portion, a corner piece and a horizontal portion of the L-type locating structure constitute a template for locating a target site and an angle locating auxiliary unit according to the invention; a hollow tube formed by the vertical portion, the corner piece and the horizontal portion is the auxiliary tunnel of the angle locating auxiliary unit according to the invention; a treatment device which is corresponding to the position of a pulmonary nodule is configured at the horizontal end of the hollow tube.

In this example, CT scan in S1 is implemented for labelling and calculating location, size, depth and number of the GGO within the lung of the patient. A method for designing the L-type locating structure model in S2 comprises:

a. a localization path which passes through the pulmonary mass and has the shortest distance front a thoracic cavity surface or an organ surface is designed on the digital model of rite thoracic cavity and the lung with pulmonary mass; a point on an organ surface is set as a puncture point according to the localization path, wherein a position of a puncture point is set according to a position of a micro incision; taking a thoracic cavity surface mark or an organ surface mark of the patient as a reference point, an anatomical orientation point is designed on the digital model of the thoracic cavity and the lung with pulmonary mass for assisting the intracorporal target site locating structure in properly placing and locating; additionally, the anatomical orientation point corresponds to a thorax surface or a suprasternal fossa around a micro incision of the patient; the auxiliary tunnel formed by the hollow tube is located in the localization path;

b. in accordance with the anatomical orientation point, the localization path and the puncture point, a graphic outline of L-type locating structure model is depicted on the organ surface of the digital model of the thoracic cavity and the lung with pulmonary mass;

c. the computer-aided design software is used to design the L-type locating structure model which closely fits a surface of the digital model of the thoracic cavity and the lung with pulmonary mass based on the depicted graphic outline.

The auxiliary tunnel of the vertical portion in S2 is configured in the localization path between the pulmonary mass and the puncture point, wherein the localization path having the shortest distance is configured for detouring around important blood vessels, nerves and bones in the digital model of the thoracic cavity and the lung with pulmonary mass under the instruction of a surgeon. Furthermore, conformally imbedding the L-type locating structure into a thoracic cavity of the patient in S4 is carried out in case of lateral pulmonary collapse; labelling and locating a pleural surface with GGO is carried out in case of lateral pulmonary ventilation and lung recruitment maneuvers, and the treatment device is located by a color market or an electric burning marker.

In this example, the L-type locating structure is a 3D printed hollow tube in "L" shape, and it comprises a vertical portion, a corner piece and a horizontal portion, wherein a head end which fits top surface of the thoracic cavity of a patient is configured on the top of the vertical portion, the end of the horizontal portion is sealed and a treatment device which is connected with the hollow tube is configured on the horizontal portion. In use, the L-type locating structure is conformally imbedded into a thoracic cavity of the patient and fixed, and the treatment device is utilized in vitro to label a position of GGO.

Figure 5:
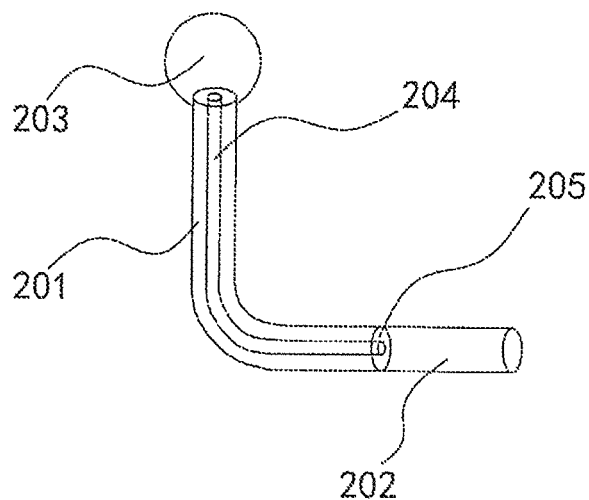
FIG. 5 is a structure diagram of an L-type locating structure within a thoracic cavity used in endoscopic surgery according to a preferred embodiment of the invention.
Figures 6, 7:
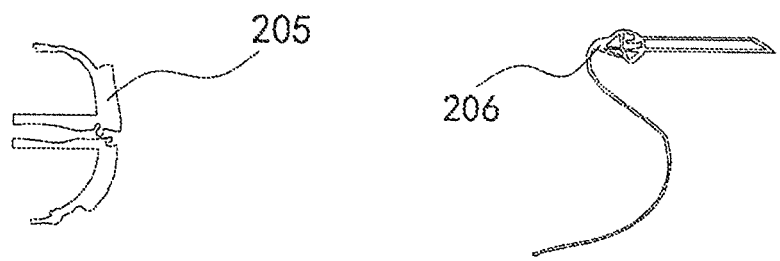
FIG. 6 is a sectional view of a horizontal portion of an L-type locating structure within a thoracic cavity used in endoscopic surgery according to a preferred embodiment of the invention, showing a locating point on the horizontal portion.
FIG. 7 is a structure diagram of a locating needle of an L-type locating structure within a thoracic cavity used in endoscopic surgery according to a preferred embodiment of the invention.

As shown in FIG. 5-6, specifically, the L-type locating structure has an "L" shape, and it comprises a pre-designed and printed hollow tube 204, with a circular cross section, an external diameter of 1-3 cm and an internal diameter of 0.5 cm. The L-type locating structure comprises a vertical portion 201, a corner piece and a horizontal portion 202; the hollow tube 204 is configured within the vertical portion 201, the corner piece and the horizontal portion 202. The L-type locating structure comprises a fixing portion and a locating portion 205 classified according to function; specifically, the vertical portion 201, the corner piece and a cylinder of the horizontal portion 202 of the L-type locating structure are the fixing portion, the hollow tube 204 and the treatment device on the horizontal portion 202 are the locating portion 205.

The top of the vertical portion 201 of the L-type locating structure provided by this example has the head end 203 which fits top surface of the thoracic cavity of a patient, wherein the head end 203 is designed in accordance, with the top surface shape of the thoracic cavity of the 3D reconstruction model of the lung of a patient; the top surface of the thoracic cavity corresponds to a position of the apex pulmonis in filling lung with air, wherein the position is located 2-3 cm above a clavicle medial segment; the head end 203 could be conformally imbedded into a thoracic cavity and fixed and fitted the top surface of the thoracic cavity in case of pulmonary collapse. The vertical portion 201 is a cylindrical hollow tube, with an external diameter of 1-3 cm and an internal diameter of 0.5 cm and a length designed in accordance with 3D reconstruction model of a thoracic cavity of a patient; the vertical portion 201 is connected to the head end 203 at the upper end and connected to the corner piece at the bottom end, and the vertical portion 201 could be placed against or parallel to the spine.

The corner piece of the L-type locating structure provided by this example is a connecting structure, there is also a pre-designed and printed hollow tube 204 in the corner piece; the corner piece has a circular cross section, an external diameter of 1-3 cm and an internal diameter of 0.5 cm; the corner piece, radian and angle of which is designed in accordance with 3D reconstruction model of the lung of the patient, is connected to the vertical portion 201 at the upper end and connected to the horizontal portion 202 at the bottom end.

The horizontal portion 202 of the L-type locating structure provided by this example also has a pre-designed and printed hollow tube 204 therein, with an external diameter of 1-3 cm and an internal diameter of 0.5 cm and a length designed in accordance with 3D reconstruction model of a thoracic cavity of a patient; one end of the horizontal portion 202 is connected to the corner piece, and the other end of it is scaled. A locating point could be configured on the horizontal portion 202 based on the position of the GGO of the patient, and a treatment device is configured on the locating point, wherein the treatment device is connected with the hollow tube 204 of the L-type locating structure and it could be a locating needle 206. As shown in FIG. 7, the locating needle 206 has an external diameter of 0.5 mm, an internal diameter of 0.4-0.45 mm and a length of 1.5-2 cm. A medical color developing agent is added into a hollow tube of the locating needle, after reaching the desired position, dyeing locating is completed by inserting the locating needle 206 into a visceral pleura corresponding to projected GGO. The locating needle 206 may be designed as an ejection component connected to an assembled biopsy gun or an ejection component of a disposable blood taking syringe for blood glucose, wherein a trigger could be used to control a needle ejector system for the locating needle piercing through the GGO. Furthermore, the treatment device may be an electrode patch, and the hollow tube 204 of the L-type locating structure may be filled with batteries or wires, after reaching the desired position, labelling and locating is completed by activating current on a visceral pleura corresponding to projected GGO for electric burning.

In this example, a method for producing the L-type locating structure comprises following steps:

S1: a computer-aided design software is used for building a digital model of the thoracic cavity and the lung with pulmonary mass of the patient in accordance with a pretreated tomographic image data of the thoracic cavity showing GGO, and the position of the GGO is determined based on the digital model of the thoracic cavity and the lung with pulmonary mass;

S2: the computer-aided design software is reused to design a fitting L-type locating structure model comprising a head end, vertical portion, a corner piece and a horizontal portion based on the digital model of the thoracic cavity and the lung with pulmonary mass, according to pre-calculated radian and angle of the corner piece, wherein the radian of the corner piece is determined by the position of the GGO and the top surface of the chest in the digital model;

S3: the L-type locating structure model is imported into a 3D printer and 3D printed, then a treatment device which is communicated with the hollow tube is mounted on the printed horizontal portion, so that the L-type locating structure is produced, wherein the position of the treatment device is determined by the position of the GGO on the horizontal portion in the digital model.

When there is a need for using the L-type locating structure in this example to locate GGO in a thoracic cavity, localization, size, depth and number of the GGO of a patient are labeled and calculated through CT scanning chest of a patient before surgery; based on the chest CT data, a software supporting 3D printing technology, such as 3Dmax, PROE, UG, AUTOCAD, SOLIDWORK is used for building a digital model of the thoracic cavity and the lung with GGO of the patient, the location of GGO is detected based on the digital model, and the abovementioned L-type locating structure is designed according to the 3D reconstruction model and it is produced by 3D printing technology.

Figure 8:
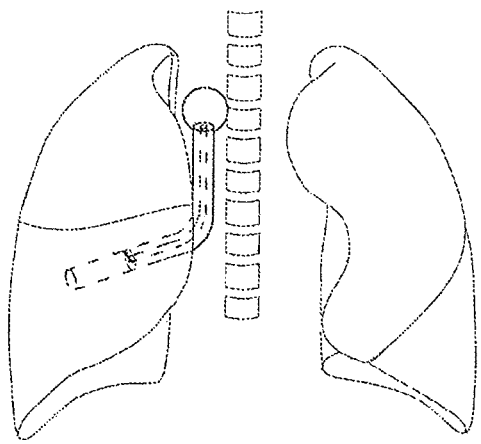
FIG. 8 is a use state diagram of an L-type locating structure within a thoracic cavity used in endoscopic surgery according to a preferred embodiment of the invention.

As shown in FIG. 8, the localization and treatment process of the L-type locating structure comprises: a patient is subjected to chest CT while filling lung with air before surgery, a software supporting 3D printing technology is used for building a digital model of the thoracic cavity and the lung with GGO of the patient, the GGO location is detected based on the digital model, and the L-type locating structure suitable for the patient is designed according to the 3D reconstruction model; during surgery, the postanesthetic patient is subjected to lateral pulmonary collapse in case of one side lung ventilation, the vertical portion of the L-type locating structure is imbedded into the thoracic cavity through a incision of thoracoscopic surgery in rotating way, so that the head end 203 of the L-type locating structure fits a corresponding position which is the position if fits and is fixed at the lop surface of the thoracic capacity, or the vertical portion 201 is placed against or parallel to the spine, after reaching the desired position, a chief anesthetist implements lateral pulmonary ventilation and lung recruitment maneuvers, the treatment device of the horizontal portion 202 of the L-type locating structure may be utilized to locate at r near the determined GGO, and the visceral pleura can be labelled by a color marker or an electric burning marker, wherein the treatment device could be a locating needle 206 or an electrode patch; the position of the pulmonary nodule could be determined for endoscopic wedge resection of the lung based on the visceral pleura marker.

Application Example 2

Clinical Application of the L-Type Locating Method Using a Thoracic Cavity Used in Endoscopic Surgery According to Example 2

A female patient, aged 52, with a height of 158 cm and a weight of 50 kg, was physically examined, a ground-glass nodule 0.5*0.5 cm was found in a position 1.5 cm under a horizontal fissure of a lateral segment of a middle lobe of right lung and approximately horizontally aligning to the sixth thoracic vertebra through chest CT; followed up after 2 weeks in anti-inflammatory therapy, CT reexamination showed that the ground-glass nodule expanded to 1*1 cm rather than shrinked, so doctors decided to undergo thoracoscopic surgery. Based on the chest CT images, 3Dmax was used for building a digital model of the thoracic cavity and the lung with GGO of the patient, the GGO was located based on the digital model; the L-type locating structure was designed according to the 3D reconstruction model, and 3D printing technology was utilized to produce the L-type locating structure made from PLA. The head end was designed according to the shape of the apical segment of the superior lobe of right lung while a patient filling his/her lung with air. The vertical portion had a length of about 13 cm, equivalent to a length from the first thoracic vertebra to the sixth thoracic vertebra, with an external diameter of 1.5 cm and an internal diameter of 0.5 cm; the corner piece had a curved surface and a right angle; the horizontal portion had a length of 8 cm, the locating point was configured at a position 2 cm from the end of the horizontal portion, wherein a locating needle was configured on the locating point, with an external diameter of 0.5 mm and an internal diameter of 0.4 mm; a rubber pipe was connected to the locating needle, filled with methylene blue dye, having a length of 0.6 m, wherein one end of the rubber pipe that was connected to the locating needle could pass through the hollow tube of the L-type locating structure; before the L-type locating structure was fixed, the locating needle could be placed within the tube cavity of the horizontal portion.

Steps of using the L-type locating structure to locate GGO in a thoracic cavity of the patient include: the postanesthetic patient was subjected to one lung ventilation in horizontal position, a 3 cm surgical incision was formed by a scalpel at a position between the fourth and fifth ribs of the right lung of the patient, laparoscopic apparatuses were utilized to form surgery channel. After lateral pulmonary collapse implemented by a chief anesthetist, a rubber pipe connected with a locating needle and filled with methylene blue dye was put into a hole at the head end of the L-type locating structure, subsequently, the L-type locating structure was inserted into the thoracic cavity through the surgical incision in rotating way, and the tail end of the rubber pipe hung outside the chest incision. The head end was conformally fitted the thoracic cage surface closely by laparoscopic apparatuses, the vertical portion is placed against the thoracic vertebra, the head end aligns to the first thoracic vertebra, the corner piece aligns to the sixth thoracic vertebra, the end of the horizontal portion was directed to sternum. After reaching the desired position, a chief anesthetist implemented to fill the lung with air and lung recruitment maneuvers to the size of the 3D reconstruction model, the position where the locating point on the horizontal portion fitted the pleura of the lung surface was the target lesion marked point; the rubber pipe hung outside was pushed into the thoracic cavity quickly, and the locating needle at the other end pierced out, then it pierced through the lung surface for filling dye, and the rubber pipe was taken back, a chief anesthetist implemented lateral pulmonary collapse and used endoscopic surgery instruments to take the L-type locating structure out of the incision, a locating process was done.

Example 3

This example provides an V-type locating method within a thoracic cavity used in endoscopic surgery for GGO, comprising following steps:

S1: tomographic image data of a chest of a patient is obtained by CT scanning the chest of the patient, a computer-aided design software is used for building a digital model of the thoracic cavity and the lung with pulmonary mass of the patient based on a locating piece image of the lung, and the 3D position of the GGO is determined based on the digital model of the thoracic cavity and the lung with pulmonary mass;

S2: the computer-aided design software is reused to customized design an V-type locating structure with film model for locating GGO which closely fits a thoracic cavity surface of the digital model of the thoracic cavity and the lung with pulmonary mass based on the digital model of the thoracic cavity and the lung with pulmonary mass obtained in S1; subsequently, an angle locating auxiliary unit model is designed on the V type locating structure with film model for locating GGO according to the 3D position of the GGO determined in S1, wherein the angle locating auxiliary unit model comprises an auxiliary tunnel, a relative angle of which is jointly determined by the position of the GGO, the position of the angle locating auxiliary unit model and the position of relevant important organ or tissue;

S3: the V-type locating structure with film corresponding to characteristics of the thoracic cavity of the patient is printed by 3D printing technology and based on 3D reconstructed images, wherein a treatment device Which is specifically located based on a locating piece image is mounted on the V-type locating structure with film;

S4: the patient is subjected to lateral pulmonary collapse during surgery, pack up the V-type locating structure with film in case of one lung ventilation, and is imbedded into a thoracic cavity, wherein a locating arm fits an unfolding arm closely after a predetermined anatomical structure, finely adjusting for reaching the desired position; a chief anesthetist implements to fill the lung of the patient with air, after lung recruitment maneuvers, a film portion of the V-type locating structure with film fits on pleural surface closely; a treatment device (a medical color developing agent is added or push a button for turning on an electrode patch) is utilized to a locating point leaves a marker on the pulmonary surface. The position of the pulmonary nodule could be determined for endoscopic wedge resection of the lung based on the marker.

In this example, the V-type locating structure with film is an intracorporal pulmonary target lesion locating structure according to the invention; an unfolding arm which could be unfolded, and a locating arm of the V-type locating structure with film constitute a template for locating a target site according to the invention, the film portion is equivalent to an angle locating auxiliary unit according to the invention; a treatment device which is corresponding to the position of a pulmonary nodule is configured on the film portion in integration.

In this example, CT scanning in S1 is implemented for labelling and calculating localization, size, depth and number of the pulmonary mass within the lung of the patient. A method for designing the V-type locating structure with film model in S2 comprises:

a. a localization path which passes through the pulmonary mass and has the shortest distance from a thoracic cavity surface or an organ surface is designed on the digital model of the thoracic cavity and the lung with pulmonary mass; a point on an organ surface is set as a puncture point according to the localization path, wherein a position of a puncture point is set according to a position of a micro incision; taking a thoracic cavity surface mark or an organ surface mark of the patient as a reference point, an anatomical orientation point is designed on the digital model of the thoracic cavity and the lung with pulmonary mass for assisting the intracorporal target site locating structure in properly placing and locating; additionally, the anatomical orientation point corresponds to a thorax surface or a suprasternal fossa around a micro incision of the patient; the auxiliary tunnel formed by a tube on the film portion is located in the localization path;

b. in accordance with the anatomical orientation point, the localization path and the puncture point, a graphic outline of the V-type locating structure with film model is depicted on the organ surface of the digital model of the thoracic cavity and the lung with pulmonary mass;

c. the computer-aided design software is used to design the V-type locating structure with film model which closely fits a surface of the digital model of the thoracic cavity and the lung with pulmonary mass based on the depicted graphic outline.

The auxiliary tunnel formed by the tube on the film portion in S2 is configured in the localization path between the pulmonary mass and the puncture point, wherein the localization path having the shortest distance is configured for detouring around important blood vessels, nerves and bones in the digital model of the thoracic cavity and the lung with pulmonary mass under the instruction of a surgeon. Furthermore, conformally imbedding the V-type locating structure with film into a thoracic cavity of the patient in S4 is carried out in case of lateral pulmonary collapse; labelling and locating a pleural surface with the pulmonary mass is carried out in case of lateral pulmonary ventilation and lung recruitment maneuvers, and the treatment device is located by a color marker or an electric burning marker.

As shown in FIG. 9, the V-type locating structure with film in this example is 3D printed, and it comprises: an unfolding arm 301, which could fit the inner thoracic cage surface after unfolded in the thoracic cavity; a locating arm 302, an end of which is connected to an end of the unfolding arm 301 by a hinge, forming a "V" type structure which opens and closes in an angle; the locating arm 302 could be located at the inner thoracic cage surface and fit the pleural wall closely; a film portion 303, which is configured between the unfolding arm 301 and the locating arm 302, is permanent connected with the unfolding arm 301 and the locating arm 302, printed in integration, wherein the film portion 303 could fit the inner thoracic cage surface and the lung surface after unfolded; and a treatment device 305, which is configured on the surface of the film portion 303, is utilized to label the position of the pulmonary mass.

As shown in FIG. 10, for precise localization, the part hinged the unfolding arm 301 and the locating arm 302 is a spoon-shaped dome 304, which has a shape the same as a top surface of the chest, wherein the top surface of the chest is the position corresponding to the apex pulmonis in filling lung with air; the unfolding arm 301 and the locating arm 302 are curved, the curved surfaces of which are set in accordance with the inner surface of the thoracic cavity. A receiving slot 306 is configured in the locating arm 302, the part hinged the unfolding arm 301 and the locating arm 302 is located within the receiving slot 306.

Figure 11:
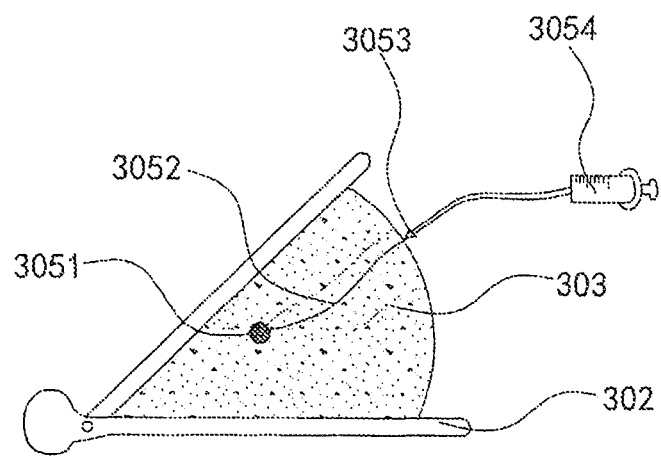
FIG. 11 shows diagrams of a locating point of a V-type locating structure with film used in endoscopic surgery according to a preferred embodiment of the invention, wherein FIG. 11-*a* is a detailed diagram of a locating point, FIG. 11-*b* is a detailed diagram of a socket, FIG. 11-*c* is a use state diagram of a fine needle.
Figure 12:
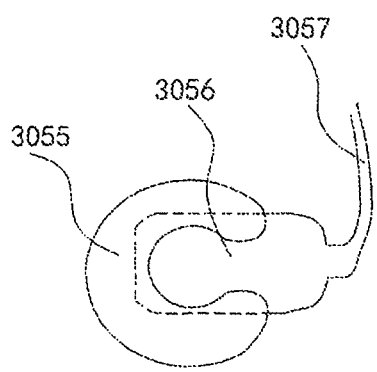
FIG. 12 shows diagrams of a locating point of a V-type locating structure with film used in endoscopic surgery according to a preferred embodiment of the invention, wherein FIG. 12-*a* is a top view of an electrode patch, FIG. 12-*b* is a section view of the electrode patch.
Figure 12:
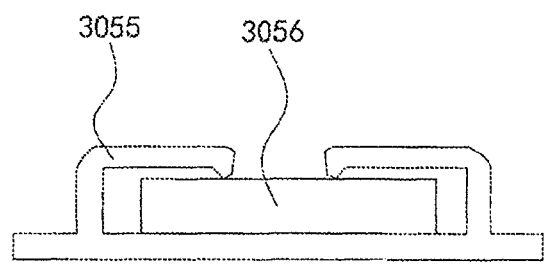

The opening and closing angle of the "V" type structure is an angle between the edge of the receiving slot and the surface of the locating arm, wherein the angle α when the unfolding arm 301 and the locating arm 302 are unfolded is set according to the position of the thoracic cavity and the pulmonary mass of the patient. A "V" type spring piece 307 is used for unfolding the unfolding arm 301 and the locating arm 302, wherein two ends of the "V" type spring piece 307 are received in a first slot 308 of the unfolding arm 301 and a second slot 300 of the locating arm 302 respectively. The treatment device 305 may be a fine needle or an electrode patch. Print materials could be selected from one or more of ABS, PLA, PVA and Nylon; if treatment device 305 is an electrode patch, the film portion 303 will be preferably heat-resisting material. In a preferred embodiment, as shown in FIG. 11, the treatment device 305 is a fine needle 3051 with length of 3-5 mm, wherein the fine needle 3051 is connected with a tube 3052 which is embedded in the film portion 303, and the tube 3052 is connected with an injection device 3054 through an adapter 3053. The injection device 3054 is a syringe, which is used to inject a medical color developing agent, preferably methylene blue dye, into the lung surface. Additionally, as shown in FIG. 12, the treatment device could be an electrode patch, comprising: a stucking slot 3055 fastened on the film portion 303 and an electrode slice 3056 mounted in the stacking slot 3055, wherein the electrode slice 3056 is connected to an electrode slice switch outside the cavity through an electric wire 3057; the electrode slice 3056 activated by the electrode slice switch could make a marker on the surface of lung by electric burning.

Specifically, both the unfolding arm 301 and the locating arm 302 are produced by 3D printing through 3Dmax in accordance with the shape of the inner thoracic cage surface of a patient, and they fit the inner thoracic cage surface closely. Specifically, after the unfolding arm 301 is unfolded within the thoracic cavity, it fits the side wall of the thoracic cavity or the front wall surface of the pleura closely; if the affected side is the right side, the locating arm 302 will fit the wall pleura closely along an angle of the spine and ribs; if the affected side is the left side, the locating arm 302 will fit the wall pleura closely along an angle of the arcus aortae, the spine and ribs.

It is regulated that a side near the head of a patient is a proximal end of the locating arm 302, the opposite side is a distal end of the locating arm 302; wherein the proximal end of the locating arm 302 is a spoon-shaped dome 304, shape of which is designed according to the shape of the thoracic apex/apex pulmonis of the patient of the 3D digital model, so that the top is located in the thoracic apex when the locating arm 302 fits the inner structure of thoracic cavity, for ensuring stability of relative position of the locating structure. The unfolding arm 301 and the locating arm 302 are joined at a point of the proximal end of the locating arm 302 through a hinge, which opens and closes in an angle. When it is folded, the unfolding arm 301 could be partly folded in the receiving slot 306 of the locating arm 302, so it is convenient for folding the V-type locating structure with film into a long strip to be sent into a body cavity through a micro incision. A first slot 308 of the unfolding arm 301 and a second slot 309 of the locating arm 302 are configured near the hinge respectively for fixing the spring piece 307, which provides a driving force for unfolding the V-type locating structure with film automatically. When the locating arm 302 is in position, the unfolding arm 301 is loosened, and the V-type locating structure with film could unfold automatically. The angle α of the the unfolding arm and the locating arm in unfolding position is an angle formed by the proximal edge of the receiving slot of the locating arm 302 and the surface of the locating arm 302; the dimension of angle α is predesigned based on data of the digital model, so as to prevent the unfolding arm 301 from unfolding excessively.

A part located between the unfolding arm 301 and the locating arm 302 is the film portion 303, shape of which is designed according to three-dimensional shape of visceral pleura of lung surface located at the angle between the unfolding arm 301 and the locating arm 302 in the digital model, the triangle film could closely attach the thoracic wall and the lung surface in a corresponding area. The treatment device 305 is configured on a side that the film portion 303 fits pulmonary tissues, the position of the treatment device 305 is the vertical projection position of the pulmonary mass on the pulmonary surface; wherein the treatment device 305 is a fine needle with a length of 3-5 min, or an electrode patch with heat-resisting material. If the treatment device 305 is a fine needle, a tube 3052 is embedded in the film portion 303, an adapter 3053 is connected with an injection device 3054, as shown in FIG. 11-*a*, 11-*b*; the injection device connected with a tube is utilized to inject a medical developer into the pulmonary surface, as shown in FIG. 11-*c*. If the treatment device 305 is an electrode patch with heat-resisting material, as shown in FIG. 12-*a*, 12-*b*, there is a stocking slot 3055, during surgery, an electrode slice 3056 could be disassembled and mounted in the stocking slot 3055, an electric wire 305 is used for activating the electrode slice 3056 outside the cavity, so as to make a marker on the surface of lung by electric burning.

In this example, a method for producing the V-type locating structure with film comprises following steps:

S1: a computer-aided design software is used for building a digital model of the thoracic cavity and the lung with pulmonary mass of a patient in accordance with a pretreated chest CT data, and the position of the pulmonary mass is determined based on the digital model of the thoracic cavity and the lung with pulmonary mass;

S2: the computer-aided design software is reused to reconstruct a fitting V-type locating structure model comprising an unfolding arm 301, a locating arm 302 and a film portion 303 based on the digital model of the thoracic cavity and the lung with pulmonary mass;

S3: the V-type locating structure model is imported into a 3D printer and 3D printed, then a spring piece 307 is mounted between printed unfolding arm 301 and locating arm 302, a treatment device 305 is mounted on a position corresponding to the film portion 303, so that the V-type locating structure with film is produced.

In the method for producing, in S2, the unfolding arm 301 of the V-type locating structure model could fit the inner thoracic cage surface of the model, the locating arm 302 of the V-type locating structure model could fit the wall pleura of the model, the film portion 303 of the V-type locating structure model could fit the inner thoracic cage surface and the pulmonary surface of the model. In S3, the position of the treatment device 305 on the film portion 303 is the vertical projection position of the pulmonary mass on the surface of the film portion 303 in the V-type locating structure model.

When there is a need for using the V-type locating structure in this example, lateral pulmonary collapse is carried out in endoscopic surgery, the V-type locating structure with film is folded in case of one lung ventilation, and it is imbedded into a thoracic cavity, wherein the locating arm 302 fits the unfolding arm 310 closely after a predetermined anatomical structure, finely adjusting for reaching the desired position, a chief anesthetist implements to fill the lung of the patient with air, after lung recruitment maneuvers, the film portion 303 of the V-type locating structure with film fits on pleural surface closely. A doctor utilizes the treatment device 305 to add a medical color developing agent or push a button for turning on an electrode patch so that the treatment device 305 leaves a marker on the pulmonary surface; the position of the pulmonary nodule could be determined for endoscopic wedge resection of the lung based on the marker.

Application Example 3

Clinical Application of the V-Type Locating Method within a Thoracic Cavity Used in Endoscopic Surgery According to Example 3

A male patient, aged 67, was physically examined, a ground-glass nodule was found in a position of the superior lobe of right lung through chest CT; CT image data was imported into a software, and a digital model of the right lung and the thoracic cage surface of the patient was restructed. The vertical projection of pulmonary nodule on the pulmonary surface was determined based on the digital model. 3Dmax was used for building a 3D digital model of the locating arm 302 according to anatomical structure of thoracic apex, spine and right lung of the patient reflected by the digital model; wherein the upper surface of the dome fitted the thoracic apex, the lower surface of it fitted the apex pulmonis; the long arm fitted an angle of the pulmonary surface, the spine and the ribs. A receiving slot, a hinge hole and a stucking slot for the spring piece are preconfigured in the locating arm 302.

Similarly, a computer-aided design software was used for drawing the unfolding arm 301 along the surface of the lung in the digital model, so that covered middle area between the unfolding arm 301 and the locating arm 302 included lung surface projection of the pulmonary nodule. A triangle area between the unfolding arm 301 and the locating arm 302 of the surface of the digital model of the right lung was selected, and the surface was separately extracted and the thickness of it was increased to 3 mm; a software was utilized to draw a hollow needle with a length of 3 mm and a diameter of 0.5 mm on a puncture point a hollow tube with a diameter of 1 mm was designed in the film, and a port was designed at the edge of the film, convenient for connecting to a infusion tube. The designed model was imported into a printed driver, material of the unfolding arm 301 and the locating arm 302 was assigned to be rigid plastics, material of the main part and the tube of the film portion was assigned to be silica gel, material of the fine needle was assigned to be rigid plastics. Three parts are printed respectively. The primal unfolding arm 301 was inserted into a corresponding position of the receiving slot of the locating arm 302; after the stainless spring piece was mounted, the edge of the film was adhered to two arms through a glue. Connection and firmness of each part were checked to ensure no product defects, then they were sent to a supply room for sterilizing and packaging for use.

During surgery, the locating structure was taken out from an aseptic package; lateral pulmonary collapse was implemented during surgery, firstly, the locating structure was folded, and it was imbedded into a thoracic cavity through a micro incision in case of one lung ventilation, the unfolding arm 301 was unfolded after the locating arm 302 fitted the predetermined anatomical structure closely, finely adjusting the locating structure for reaching the desired position; a chief anesthetist implemented to fill the affected side lung of the patient with air, after lung recruitment maneuvers, the film portion 303 of the V-type locating structure fitted on pleural surface closely, and the fine needle pierced through the pleural surface. A little methylene blue dye was injected through a syringe by a doctor, so that the locating point left a blue marker on the pulmonary surface. The lateral pulmonary collapse was implemented again, and the marker of the pulmonary surface was checked. Accurate situation of the marker was estimated based on assisted CT before surgery. When the marker was confirmed, the position of the pulmonary nodule could be determined for endoscopic wedge resection of the lung tissue based on the marker.

Example 4

This example provides a method for locating a pulmonary mass in vitro based on a 3D printed locating structure, comprising following steps:

S1: tomographic image data of a chest of a patient is obtained by CT scanning the chest of the patient, a computer-aided design software is used for building a digital model of a body surface morphology and an anatomical bony structure of the patient, and a puncture point of the body surface of the patient corresponding to the pulmonary mass is determined based on the digital model of the body surface morphology and the anatomical bony structure;

S2: the computer-aided design software is reused to customize an umbrella-shaped template model for locating a pulmonary mass which closely fits the digital model of the body surface morphology and the anatomical bony structure of the patient based on the digital model of the body surface morphology and the anatomical bony structure obtained in S1; subsequently, a center locating module model is designed on the umbrella-shaped template model for locating a pulmonary mass according to the 3D position of the pulmonary mass determined in S1, wherein the center locating module model comprises an auxiliary tunnel, a relative angle of which is jointly determined by the position of the pulmonary mass, the position of the center locating module model and the position of relevant important organ or tissue, the angle and the depth for inserting the locating needle are designed based on the same;

S3: the umbrella-shaped template model for locating a pulmonary mass with the center locating module model is printed by 3D printing technology, so as to produce an extracorporeal pulmonary mass locating structure having an auxiliary tunnel;

S4: the extracorporeal pulmonary mass locating structure produced in S3 is mounted on a corresponding position of a body surface of the patient, then a treatment device is used to correspondingly treat the pulmonary mass with the assistance of the center locating module.

In this example, in the extracorporeal pulmonary mass locating structure, the umbrella-shaped template for locating a pulmonary mass constitutes a template for locating a target site according to the invention, the center locating module constitutes an angle locating auxiliary unit according to the invention; a treatment device which is corresponding to the position of a pulmonary mass is configured on the center locating module.

In this example, CT scanning in S1 is implemented for labelling and calculating localization, size, depth and number of the pulmonary mass within the lung of the patient. A method for designing the extracorporeal pulmonary mass locating structure model in S2 comprises:

a. a localization path which passes through the pulmonary mass and has the shortest distance from a body surface is designed on the digital model of the body surface morphology and the anatomical bony structure; a point on a body surface is set as a puncture point according to the localization path; raking a body surface mark of the patient as a reference point, an anatomical orientation point is designed on the digital model of the body surface morphology and the anatomical bony structure for assisting the extracorporeal target site locating structure in properly placing and locating, wherein the anatomical orientation point corresponds to the body surface mark of the patient;

b. in accordance with the anatomical orientation point the localization path and the puncture point, a graphic outline of the template for locating a pulmonary target lesion is depicted on the body surface of the digital model of the body surface morphology and the anatomical bony structure;

c. the computer-aided design software is used to design the template model for locating a pulmonary target lesion which closely fits a surface of the digital model of the body surface morphology and the anatomical bony structure based on the depicted graphic outline.

The auxiliary tunnel of the angle locating auxiliary unit model in S2 is configured in the localization path between an anatomic locating point and the puncture point, wherein the localization path having the shortest distance is configured for detouring around important blood vessels, nerves and bones in the digital model of body surface morphology and the anatomical bony structure under the instruction of a surgeon.

When there is a need for using the extracorporeal pulmonary mass locating structure in this example, stand bars of the extracorporeal medical auxiliary apparatus for localization is attached to the corresponding position of the body surface mark of the patient, so that the extracorporeal medical auxiliary apparatus for localization closely fits the thoracic cavity of the patient, without any local stress/deformation, it is fixed on the body surface of the patient; after placed in position, a position of the center locating module is the place where the puncture needle is inserted, specifically, the puncture needle is inserted through a hole for inserting needle reserved on the center locating module, and a mark point on the the center locating module is taken as a reference, it is inserted for a certain distance along the hole for inserting needle according to pre-calculated data so as to make the needle tip to teach a position near the pulmonary mass; the position of the puncture needle is confirmed by CT scanning, no complications are found, then a hook-wire or a micro-coil is manually released, the puncture needle is pulled out, so the process of puncture localization is completed after sterilizing and bandaging; the position of the hook-wire or the micro-coil could be found easily in an endoscopy, so it is convenient for determination of lesion position, thus precisely removing diseased tissues.

Figure 13:
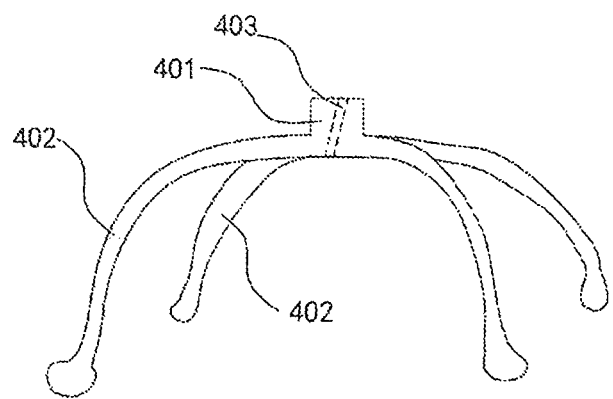
FIG. 13 is a whole structure diagram of an extracorporeal medical auxiliary apparatus for localization of a pulmonary target lesion according to a preferred embodiment of the invention.

As shown in FIG. 13, this example provides a 3D printed extracorporeal medical auxiliary apparatus for locating a pulmonary mass, which shows an umbrella shape or a spider shape or an octopus shape, comprising: a center locating module 401, in which a hole for inserting needle 403 is configured to restrict and stabilize direction of inserting a puncture needle 404 when the puncture needle 404 is labelling the pulmonary mass; and stand bars 402, which are curved, and a front end of each of stand bars 402 is permanently connected to the center locating module 401, a tail end of each of stand bars 402 is bent downwards contacting human body; there exists a plurality of stand bars 402, which support the center locating module 401, so that an umbrella-shaped structure is formed, wherein the stand bars 402 are umbrella stands, the center locating module 401 is the top, and the puncture needle 404 is the umbrella handle.

In this example, the umbrella-shaped structure comprising stand bars 402 is a template for locating a target site according to the invention, and the center locating module is an angle locating auxiliary unit according to the invention. The CT scanning in S1 comprises labelling and calculating localization, size, depth and number of the pulmonary mass.

Figure 14:
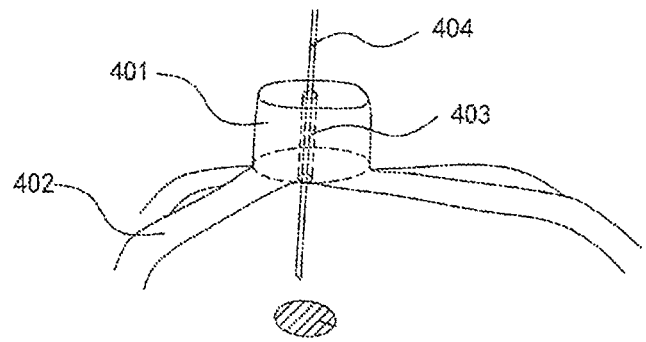
FIG. 14 is a use state diagram of an extracorporeal medical auxiliary apparatus for localization of a pulmonary target lesion according to a preferred embodiment of the invention.

As shown in FIG. 14, number of the stand bars 402 is equal or greater than 403, preferably 4; the end of each stand bar 402 is flat; the end of each stand bar 402 is located on the position of the body surface mark, which are selected from more than one of suprasternal fossa, sternal angle, xiphoid, 7th cervical vertebra, the twelfth rib of the thoracic wall of the affected side; the center locating module 401 is a cylinder or a cube, a gripping holder which is used to secure the puncture needle 404 within the hole for inserting needle 403 is configured on the center locating module 401, wherein the center locating module 401 and the stand bars 402 are molded in integration.

In this example, a method for producing the extracorporeal medical auxiliary apparatus for locating pulmonary mass comprises following steps:

S1: a computer-aided design software is used for building a digital model of the thoracic cavity and the lung with pulmonary mass of a patient in accordance with a pretreated a locating piece image showing pulmonary mass, and the projective position of the pulmonary mass on the body surface is determined based on the digital model of the thoracic cavity and the lung with pulmonary mass;

S2: the computer-aided design software is reused to reconstruct a fitting umbrella-shaped structure model comprising the stand bars 402 and the center locating module 401 based on pre-calculated angle and depth for inserting needle according to the digital model of the thoracic cavity and the lung with pulmonary mass;

S3: the umbrella-shaped structure model is imported into a 3D printer and 3D printed, so that the extracorporeal medical auxiliary apparatus for locating pulmonary mass is produced.

When there is a need for using the extracorporeal medical auxiliary apparatus for locating and treating the pulmonary mass in this example, stand bars 402 of the extracorporeal medical auxiliary apparatus are attached on the body surface of a patient according to preset, and the patient is required to take a deep breath and hold breath. Due to the extracorporeal medical auxiliary apparatus printed based on the thorax of the patient, when the extracorporeal medical auxiliary apparatus for localization closely fits the thoracic cavity of the patient, without any local stress deformation, it is fixed in position and the patient is on the right position. After placed in place, the direction of the center locating module 401 is the part for inserting the puncture needle 404. The puncture needle 404 is inserted through the hole for inserting needle 403 preformed on the center locating module 401, taking a mark point on the puncture needle 404 as a reference point, the puncture needle 404 is inserted in a certain depth in accordance with pre-calculated data and the track of the hole for inserting needle 403, so as to make the needle tip to reach a position near the pulmonary mass. As shown in FIG. 14, a gripping holder of the center locating module 401 is used to secure the puncture needle 404 within the hole for inserting needle 403. Thereafter, the position of the puncture needle is confirmed by CT scanning, no complications are found, then a hook-wire or a micro-coil is manually released, the puncture needle 404 is pulled out, so the process of puncture localization is completed after sterilizing and bandaging. The position of the hook-wire or the micro-coil could be found easily in an endoscopy, so it is convenient for determination of lesion position, thus precisely removing diseased tissues.

Application Example 4

Clinical Application of the Method for Locating a Pulmonary Mass In Vitro Based on a 3D Printed Locating Structure According to Example 4

A male patient, aged 65, was physically examined, a ground-glass nodule was found in a position of the middle lobe of right lung through chest CT, CT before surgery of the patient was utilized to reconstruct a digital model of the chest. The projection of pulmonary nodule on the body surface was found between the fourth rib and the fifth rib of the right anterior axillary line by the digital model. A plane tangent to the thoracic cavity of the patient was considered as a reference horizontal plane, a puncture point on the body surface was considered as an original point, and a three-dimensional system of coordinate was set; wherein the positive direction of X axis was approximately from the tail end of the patient to the head end of the patient, the positive direction of Y axis was approximately from the dorsal side of the patient to the ventral side of the patient, the positive direction of Z axis was approximately from the interior side of the patient to the outer side of the patient. Angles between the direction of inserting needle and X, Y, Z axis were respectively 41°, 49°, 7°, and the depth of inserting needle was 5 cm relative to the puncture point.

3Dmax was used for building a digital model of the structure, wherein five stand bars were attached to the thoracic wall of the patient, with a width of 1.5 cm and a length of 1 cm; each end of them respectively corresponded to suprasternal fossa, sternal angle, xiphoid, the seventh spinous process of cervical vertebra and angle of intersection between the twelfth rib on the right and the spine; five stand bars 402 were gathered at the puncture point of the body surface, namely the center locating module 401. The center locating module was a cylinder, with a height of 3 cm and a diameter of 3 cm, it was connected with five stand bars 402. A hole was preformed through the upper surface to lower surface of the center locating module, with a diameter of 21G, an angle of the hole was the same as that of inserting needle as described above, a lower end of the hole corresponded to a puncture point of the body surface, a top end of the hole corresponded to a hole for inserting needle. The produced 3D digital model was imported into a printer driver, raw material was assigned to be rigid transparent material through layering analysis and internal structure calculation, a final product model was printed by hot melt layer depositing; then the final product was sent to a supply room of a hospital for ethylene oxide sterilizing and packaging for use.

When the extracorporeal medical auxiliary apparatus for localization according to this example was used for labelling and treating pulmonary mass, the patient laid himself flat on a CT bed, wherein the thoracic cage was fully exposed, and the right thoracic cage was sterilized routinely before surgery. A surgeon used sterile gloves to take the extracorporeal medical auxiliary apparatus for localization out from an aseptic bag; the extracorporeal medical auxiliary apparatus for localization was mounted on the right thoracic wall of the patient, stand bars 402 were placed on positions corresponding to the body markers; after the patient was required to take a deep breath, the surgeon checked that alignment of each body marker was good, without abnormal stress on any stand bar, so the extracorporeal medical auxiliary apparatus for localization could tightly attached the thoracic cage of the patient. The surgeon took a puncture needle out, and re-checked the position of the extracorporeal medical auxiliary apparatus for localization before operation, then used a palpation method to determine that whether the center locating module 401 was located above the rib or under the edge of the rib and close to nervus vascularis; the puncture needle was inserted along the angle of the preformed hole slowly until it reached the predetermined depth for inserting needle; the extracorporeal medical auxiliary apparatus for localization was taken down, and the position of the puncture needle was determined to be good without further adjustment by CT scanning, so a micro-coil was released and the puncture needle was pulled out, disinfecting and packaging routinely, no complications were found after half an hour observation, so the patient was moved back to a sickroom, waiting for a selective operation.

Example 5

This example provides a method for locating and treating a pulmonary target lesion in vitro, more convenient and more accurate than the methods described in Example 1-4, comprising following steps:

S1: a computer-aided design software is used for building a digital model of a body surface morphology and an anatomical bony structure of a patient in accordance with pretreated CT image sequence showing a pulmonary mass, and a projective position of the pulmonary mass on the body surface is determined based on the digital model of the body surface morphology and the anatomical bony structure;

S2: the computer-aided design software is reused to design a triangular or butterfly-shaped template model for locating the pulmonary mass which closely fits a body surface of the digital model of the body surface morphology and the anatomical bony structure of the patient based on the digital model of the body surface morphology and the anatomical bony structure obtained in S1; subsequently, an angle locating auxiliary unit model is designed on the triangular or butterfly-shaped template model for locating the pulmonary mass according to the 3D position of the pulmonary mass determined in S1, wherein the angle locating auxiliary unit model comprises an auxiliary tunnel, a relative angle of which is jointly determined by the position of the pulmonary mass the position of the center locating module model and the position of relevant important organ or tissue, the angle and the depth for inserting the locating needle are designed based on the same; an upward-fovea of a body sternum, an upper edge connecting line of a body sternoclavicular joint, an anterior median line, sternal angle and xiphoid are set as body surface markers on the digital model of the body surface morphology and the anatomical bony structure, the template model for locating a pulmonary target lesion is depicted on the body surface of the digital model of the body surface morphology and the anatomical bony structure; the template model for locating a pulmonary target lesion and the angle locating auxiliary unit model constitute a digital model of the extracorporeal medical auxiliary apparatus for localization/biopsy;

S3: the digital model of the extracorporeal medical auxiliary apparatus for localization/biopsy obtained in S3 is imported into a 3D printer and printed integrally, so as to produce an extracorporeal medical auxiliary apparatus for localization/biopsy, which is the template for locating the target site according to the invention;

S4: the extracorporeal medical auxiliary apparatus for localization/biopsy produced in S3 is mounted on a corresponding position of a body surface of the patient, then a treatment device is used to correspondingly treat the pulmonary mass with the assistance of the angle locating auxiliary unit.

In this example, in the extracorporeal medical auxiliary apparatus for localization/biopsy, the triangular or butterfly-shaped template for locating a pulmonary mass is a template for locating a target site according to the invention, a treatment device which is corresponding to the position of a pulmonary mass is configured on the center locating module.

In this example, CT scanning in S1 is implemented for labelling and calculating localization, size, depth and number of the pulmonary mass within the lung of the patient. A method for designing the triangular or butterfly-shaped template model for locating structure in S2 comprises:

a. a localization path which passes through the pulmonary mass and has the shortest distance from a body surface is designed on the digital model of the body surface morphology and the anatomical bony structure; a point on a body surface is set as a puncture point according to the localization path; taking a body surface mark of the patient as a reference point, an anatomical orientation point is designed or the digital model of the body surface morphology and the anatomical bony structure for assisting the extracorporeal target site locating structure in properly placing and locating, wherein the anatomical orientation point corresponds to the body surface mark of the patient; wherein the body surface mark could be suprasternal fossa, an upper edge connecting line of a body sternoclavicular joint, anterior median line, sternal angle and xiphoid;

b. in accordance with the anatomical orientation point, the localization path and the puncture point, a graphic outline of the template for locating the pulmonary target lesion is depicted on the body surface of the digital model of the body surface morphology and the anatomical bony structure;

c. the computer-aided design software is used to design the triangular or butterfly-shaped template for locating the pulmonary mass which closely fits a surface of the digital model of the body surface morphology and the anatomical bony structure based on the depicted graphic outline.

The auxiliary tunnel of the angle locating auxiliary unit model in S2 is configured in the localization path between an anatomic locating point and the puncture point, wherein the localization path having the shortest distance is configured for detouring around important blood vessels, nerves and bones in the digital model of body surface morphology and the anatomical bony structure under the instruction of a surgeon.

Figure 15:
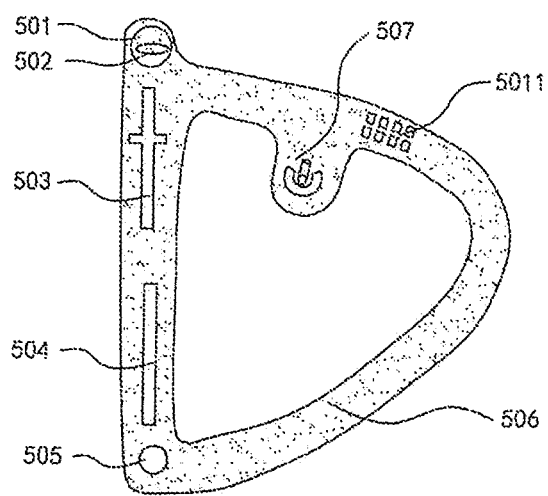
FIG. 15 is a structure diagram of a triangular extracorporeal medical auxiliary apparatus for localization/biopsy of a pulmonary target lesion according to a preferred embodiment of the invention.
Figure 16:
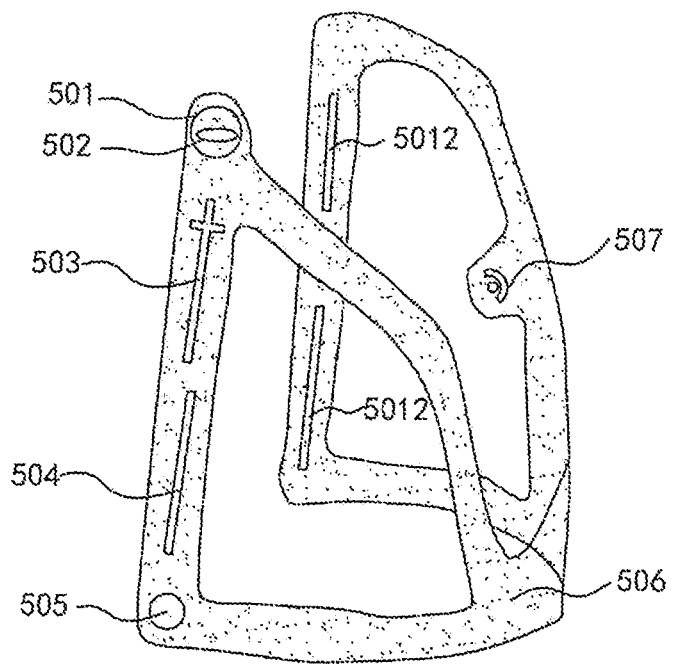
FIG. 16 is a structure diagram of a butterfly extracorporeal medical auxiliary apparatus for localization/biopsy of a pulmonary target lesion according to a preferred embodiment of the invention.
Figure 17:
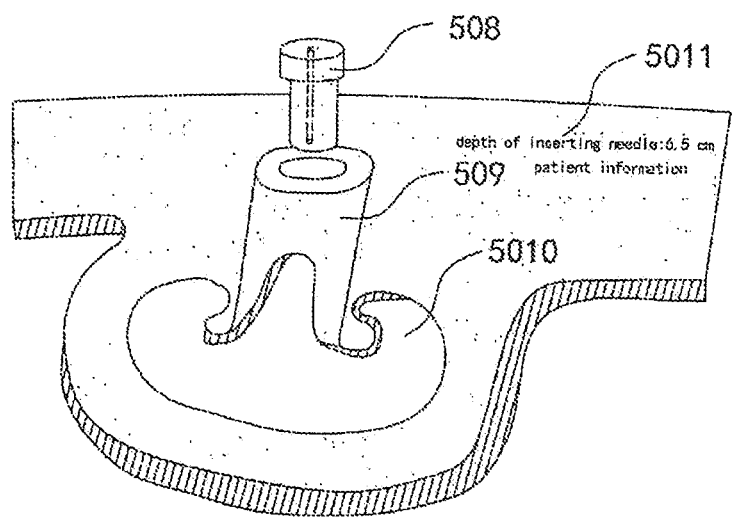
FIG. 17 is a structure diagram of an angle locating auxiliary unit of an extracorporeal medical auxiliary apparatus for localization/biopsy of a pulmonary target lesion according to a preferred embodiment of the invention.
Figure 18:
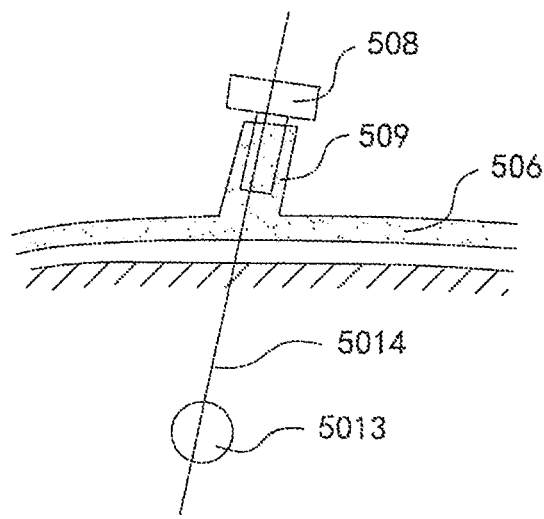
FIG. 18 is a structure diagram of a needle passage of an extracorporeal medical auxiliary apparatus for localization/biopsy of a pulmonary target lesion according to a preferred embodiment of the invention.

As shown in FIG. 15-16, the extracorporeal medical auxiliary apparatus for localization/biopsy according to this example is 3D printed in an integral form, comprising: a template 506 for locating the pulmonary target lesion, which is a triangular or butterfly-shaped structure fitting the body surface, several bulges 501 and/or hollow holes corresponding to body surface markers are configured thereon, based on the overall structure, the triangular or butterfly-shaped template 506 for locating the pulmonary target lesion is curved, so as to fit the body surface better; and an angle locating auxiliary unit 507 configured on the template 506 for locating the pulmonary target lesion, as shown in FIG. 17, consisted of a guide rail for inserting needle 508, a guide rail receiving column 509 and a sterilizing anesthesia hole 5010, wherein the guide rail receiving column 509 is a cylindrical hollow structure mounted on the template 506 for locating the pulmonary target lesion, the sterilizing anesthesia hole 5010 is set on a joint pan between the guide rail receiving column 509 and the template 506 for locating the pulmonary target lesion, and the guide rail for inserting needle 508 is a hollow structure and detachably mounted on the upper end of the guide rail receiving column 509 so that a puncture needle can pass through an auxiliary tunnel formed by the guide tail for inserting needle 508 and the guide rail receiving column 509; wherein the auxiliary tunnel is a path for inserting needle, as shown in FIG. 18, the puncture needle passes through a path for inserting needle 5014 and penetrates into a target lesion 5013.

In practice, there exist three pathways for inserting a puncture needle into thoracic cavity in accordance with different positions of pulmonary lesion, including: inserting a puncture needle from dorsal side, inserting a puncture needle from anterior chest wall, inserting a puncture needle from lateral chest wall. With respect to inserting a puncture needle from dorsal side, a patient is in lateral position during puncture, the 3D printed extracorporeal medical auxiliary apparatus for localization/biopsy of pulmonary target lesion according to the invention is designed to be a butterfly-shaped structure (twin wings), as shown in FIG. 16; With respect to inserting a puncture needle from anterior chest wall and inserting a puncture needle from lateral chest wall, a patient is in supine position during puncture, the 3D printed extracorporeal medical auxiliary apparatus for localization/biopsy of pulmonary target lesion according to the invention is designed to be a triangular structure (single wing), as shown in FIG. 15. The abovementioned design could not only ensure stability of placement of the template 506 for locating a pulmonary target lesion, but also make the best use of the body surface marker of anterior chest wall when the patient is in lateral position, and avoid deformation and dislocalization of the template 506 for locating the pulmonary target lesion due to physical pression when the patient is in supine position.

In this example, a hollow hole comprises: a hollow line 502, located on the frame of the template 506 for locating the pulmonary target lesion, corresponding to an upper edge connecting line of a body sternoclavicular joint, a cross hollow line 503 corresponding to an anterior median line and a horizontal line of the sternal angle, a hollow line 504 corresponding to an anterior median line, and a circular hollow hole 505, located at a top of the template 506 for locating the pulmonary target lesion, corresponding to a xiphoid of the body, or a hollow line 5012 corresponding to a posterior median line; and the bulges 501 are configured at another top of the template 506 for locating the pulmonary target lesion, corresponding to a suprasternal fossa of the body. Separate configuration of the hollow line 504 corresponding to an anterior median line and the cross hollow line 503 corresponding to an anterior median line and a horizontal line of the sternal angle is intended to enhance strength of the scaffold and avoid a fragile front structure caused by an overlong hollow line, wherein the cross hollow line 503 corresponding to an anterior median line and a horizontal line of the sternal angle consists of a vertical hollow line corresponding to an anterior median line and a horizontal hollow line corresponding to a horizontal line of the sternal angle.

As shown in FIG. 15-16, an angle locating auxiliary unit 507 is configured on an inward extension part of the template 506 for locating the pulmonary target lesion, and this configuration can ensure stability of placement when the puncture needle is inserting.

As shown in FIG. 17, the guide rail for inserting needle 508 is a hollow bolt-like structure, made of stainless steel, convenient for sterilization under high temperature and high pressure. The lower end of the guide rail for inserting needle 508 could ho inserted into a hollow cavity of the guide rail receiving column 509; and an upper end of the guide rail for inserting needle 508 is a cap structure, configured to prevent itself from sliding into the hollow cavity of the guide rail receiving column 509, convenient for assembly and removal. An angle of the guide rail receiving column 509 is designed according to the abovementioned method, it is connected with the template 506 for locating a pulmonary target lesion, printed in an integral form. Furthermore, for the convenience of local anesthetic injection after safe placement, the sterilizing anesthesia hole 5010 is set on the side and around the bottom of the guide rail receiving column 509, showing a semilunar open structure.

In this example, a lettering 5011 is carved on a surface of the template 506 for locating the pulmonary target lesion near the angle locating auxiliary unit 507, displaying information such as the angle and/or the depth of inserting needle, and patient information.

The present invention also provides a method for producing the 3D printed extracorporeal medical auxiliary apparatus for localization/biopsy of pulmonary target lesion, which mainly uses CT image data of a patient, which obtained when he/she is admitted to hospital, and a computer-aided design software is used for building a digital model of a body surface morphology and an anatomical bony structure of a patient; suprasternal fossa, an upper edge connecting line of a body sternoclavicular joint, anterior median line, sternal angle and xiphoid are considered as body surface markers, the digital model of the locating structure is depicted based on a body surface morphology and an anatomical bony structure of the patient; after detouring around important blood vessels, nerves and bones, a puncture point of a lesion on a body surface is taken as the point for inserting needle, and a connecting line between them is set as an entry path, a distance from the center of the target lesion to the superior border of the guide rail for inserting needle is set as an inserting needle depth, then the entry path for inserting needle and the guide rail receiving column are designed, a computer-aided design software is reused to reconstruct a fitting angle locating auxiliary unit model on the template model for locating a pulmonary target lesion; the template model for locating a pulmonary target lesion and the angle locating auxiliary unit model constitute a digital model of the extracorporeal medical auxiliary apparatus for localization/biopsy, then the extracorporeal medical auxiliary apparatus for localization/biopsy is 3D printed by 3D printing technology, comprising following steps:

S1: a computer-aided design software is used for building a digital model of the body surface morphology and the anatomical bony structure of a patient in accordance with pretreated CT image sequence showing a pulmonary mass, and a projective position of the pulmonary mass on the body surface is determined based on the digital model of the body surface morphology and the anatomical bony structure;

S2: suprasternal fossa, an upper edge connecting line of a body sternoclavicular joint, anterior median line, sternal angle and xiphoid are considered as body surface markers based on the digital model of the body surface morphology and the anatomical bony structure, the template model 506 for locating a pulmonary target lesion is depicted based on a body surface morphology and an anatomical bony structure of the patient;

S3: the computer-aided design software is reused to reconstruct a fitting angle locating auxiliary unit model 507 on the template model 506 for locating a pulmonary target lesion based on pre-designed angle and depth for inserting needle, wherein the template model 506 for locating a pulmonary target lesion and the angle locating auxiliary unit model 507 constitute a digital model of the extracorporeal medical auxiliary apparatus for localization/biopsy;

S4: the digital model of the extracorporeal medical auxiliary apparatus for localization/biopsy produced in S3 is imported into a 3D printer and 3D printed, so that the extracorporeal medical auxiliary apparatus for localization/biopsy is produced.

In the method of producing the extracorporeal medical auxiliary apparatus for localization/biopsy, the computer-aided design software in S1 is selected from Mimics, Magics, Geomagic Studio, 3Dmax, PROE, UG, AUTOCAD and SOLID WORK. The method for calculating angle and depth for inserting needle in S3 comprises; after detouring important blood vessels, nerves and bones, a puncture point of a lesion on a body surface is taken as the point for inserting needle, a connecting line between the point for inserting needle and the lesion is taken as an entry path for inserting needle, a distance from the lesion center to a superior border of the guide rail for inserting needle 508 is taken as the depth for inserting needle. Materials for 3D printing the extracorporeal medical auxiliary apparatus for localization/biopsy in S4 could be selected from one or more of metal, ABS, PLA, PVA and Nylon.

When there is a need for using the extracorporeal medical auxiliary apparatus for localization/biopsy of a pulmonary target lesion in this example, the template model 506 for locating a pulmonary target lesion of which is attached on the body surface of a patient according to preset, and each body surface marker point and each structure aligns to a corresponding hollow hole or bulge, the apparatus is fixed on the thoracic cage of the patient by using medical adhesive tape, then the patient is required to take a deep breath and hold breath. Due to the template model 506 for locating a pulmonary target lesion printed based on the shape of the thoracic cage of the patient, when the apparatus closely fits the thoracic cage of the patient, without any local stress/deformation, it is fixed in position and the patient is on the right position. After placed in place, sterilizing with alcohol is implemented to the puncture site through the sterilizing anesthesia hole 5010, then sterilized guide rail for inserting needle 508 is inserted into the hollow cavity of the guide rail receiving column 509, wherein a hollow tunnel formed by the guide rail for inserting needle 508 and the guide rail receiving column 509 is the path for inserting the puncture needle. The puncture needle is inserted through a hole for inserting needle preformed on the guide rail for inserting needle 508, taking a depth scale on the puncture needle as a reference, the puncture needle is inserted in a certain depth in accordance with pre-calculated data and the track of the hole for inserting needle, so as to make the needle tip to reach a position near the pulmonary mass.

Thereafter, the position of the puncture needle is confirmed by CT scanning, no complications are found, then a hook-wire or a micro-coil is manually released, the puncture needle is pulled out, so the process of puncture localization is completed after sterilizing and bandaging. The position of the hook-wire or the micro-coil could be found easily under thoracoscope, so it is convenient to confirm the position of lesion, thus precisely removing diseased tissues.

Application Example 5

Clinical Application of the Method for Locating and Treating a Pulmonary Target Lesion In Vitro According to Application Example 5

Figure 19:
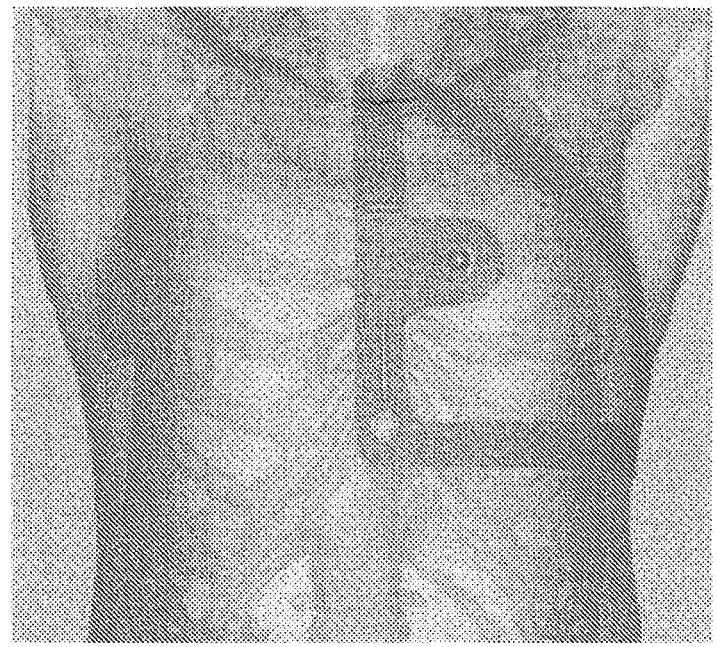
FIG. 19 is a diagram of a triangular extracorporeal medical auxiliary apparatus for localization/biopsy and a digital model of a body surface morphology and an anatomical bony structure according to a preferred embodiment of the invention.

A female patient, aged 65, was physically examined, a ground-glass nodule was found in a position of left lung through chest CT, a puncture localization was proposed; as shown in FIG. 19, CT before surgery of the patient was utilized to reconstruct a digital model of the chest. After measurement and design, the projection of pulmonary nodule on the body surface was found between the fourth rib and the fifth rib of the left midclavicular line according to the digital model, it was scheduled to insert a needle from anterior chest wall.

3Dmax was used for building a digital model of the structure, wherein three sides of the triangular structure (single wing) for localization/biopsy were attached to the thoracic wall of the patient, with a width of 3 cm and a thickness of 0.3 cm; wherein one side along the sternum depicted depressions for locating and hollow lines respectively corresponding to suprasternal fossa, sternal angle, anterior median line and xiphoid according to anatomical structure, the angle locating auxiliary unit was also attached to this side; the other two sides along the body surface morphology of the thoracic cage of the patient would increase the stability of the device placement. A puncture point of a lesion on a body surface was taken as the point for inserting needle, a connecting line between them was taken as an entry path for inserting needle, a distance from the lesion center to a superior border of the guide rail for inserting needle was taken as the depth for inserting needle, the entry path for inserting needle and the guide rail receiving column were designed; after all design completed, a 3D digital model file was generated and the generated 3D digital model was imported into a printer driver, raw material was assigned to be Nylon powder through layering analysis and internal structure calculation, a final product which was the structure model for localization/biopsy was printed by hot melt layer depositing; then the printed medical auxiliary apparatus for localization/biopsy was sent to a supply room of a hospital for ethylene oxide sterilizing and packaging in an aseptic bag for use, wherein the guide rail for inserting needle could be sterilized under high temperature and high pressure and packaged in an aseptic bag for use.

Figure 20:
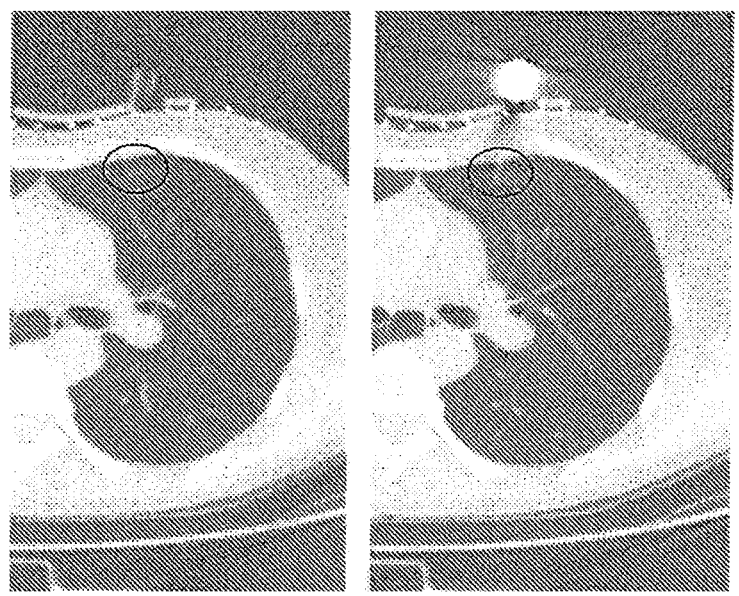
FIG. 20 is a comparison diagram of puncture effect in CT reexamination in Application Example 5 of the invention.

The patient laid herself flat on a CT bed, wherein the thoracic cage was fully exposed, an assistant depicted the positions of suprasternal fossa, sternal angle, anterior median line and xiphoid of the patient by a marking pen. The medical auxiliary apparatus was taken out from an aseptic bag, and it was fixed on the body of the patient by elastic straps. The thoracic surgeon checked that alignment of each locating point was good, without abnormal stress on each side of the apparatus, so the medical auxiliary apparatus could tightly attached the thoracic cage of the affected side of the patient. The thoracic surgeon confirmed patient information, and determined the depth for inserting needle; the position of the apparatus was determined to be good without further adjustment by CT scanning, so the assistant made a routine sterilizing to an area to be pierced before surgery, a thoracic surgeon used sterile gloves to take a puncture needle out; after the patient was required to take a deep breath, the puncture needle was inserted in a predetermined depth for inserting needle in accordance with the preformed hole on the guide rail for inserting needle; so a locating hook was released, the puncture needle wax pulled out, disinfecting and packaging routinely; CT reexamination showed that the lesion was hit. No complications were found after half an hour observation, so the patient was moved back to a sickroom, waiting for a surgery, as shown in FIG. 20, CT reexamination confirmed that the path for inserting needle was accurate and the process of puncture was successful.

Application Example 6

Clinical Application of the Method for Locating and Treating a Pulmonary Target Lesion In Vitro According to Example 6

Figure 21:
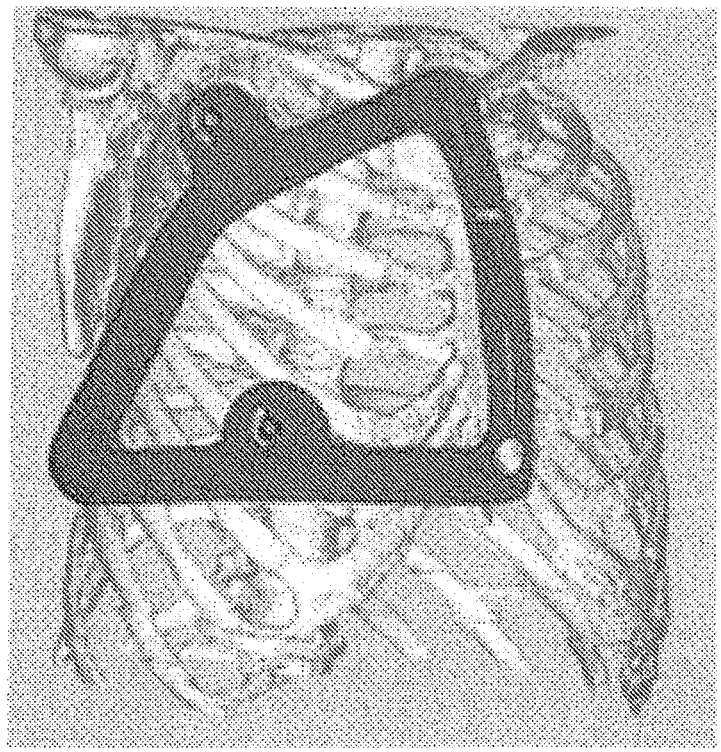
FIG. 21 is a diagram of a triangular extracorporeal medical auxiliary apparatus for localization/biopsy and a digital model of a body surface morphology and an anatomical bony structure in Application Example 6 of the invention.

A female patient, aged 61, was physically examined, two ground-glass nodules were found in a position of right lung through chest CT, a puncture localization was proposed; as shown in FIG. 21, CT before surgery of the patient was utilized to reconstruct a digital model of the chest. After measurement and design, the projections of pulmonary nodules on the body surface were respectively found between the first rib and the second rib of the right close to anterior axillary line, and between the fifth rib and the sixth rib of the same according to the digital model, it was scheduled to insert a needle from anterior lateral chest wall.

3Dmax was used for building a digital model of the structure, wherein three sides of the triangular structure (single wing) for localization/biopsy were attached to the thoracic wall of the patient, with a width of 3 cm and a thickness of 0.3 cm; wherein one side along the sternum depicted depressions for locating and hollow lines respectively corresponding to suprasternal fossa, sternal angle, anterior median line and xiphoid according to anatomical structure; the other two sides along the body surface morphology of the thoracic cage of the patient were also attached to the angle locating auxiliary unit. A puncture point of a lesion on a body surface was taken as the point for inserting needle, a connecting line between them was taken as an entry path for inserting needle, a distance from the lesion center to a superior border of the guide rail for insetting needle was taken as the depth for inserting needle, the entry path for inserting needle and the guide rail receiving column were designed; after all design completed, a 3D digital model file was generated and the generated 3D digital model was imported into a printer driver, raw material was assigned to be Nylon powder through layering analysis and internal structure calculation, a final product which was the structure model for localization/biopsy was printed by hot melt layer depositing; then the printed medical auxiliary apparatus for localization/biopsy was sent to a supply room of a hospital for ethylene oxide sterilizing and packaging in an aseptic bag for use, wherein the guide rail for inserting needle could be sterilized under high temperature and high pressure and packaged in an aseptic bag for use.

Figure 22:
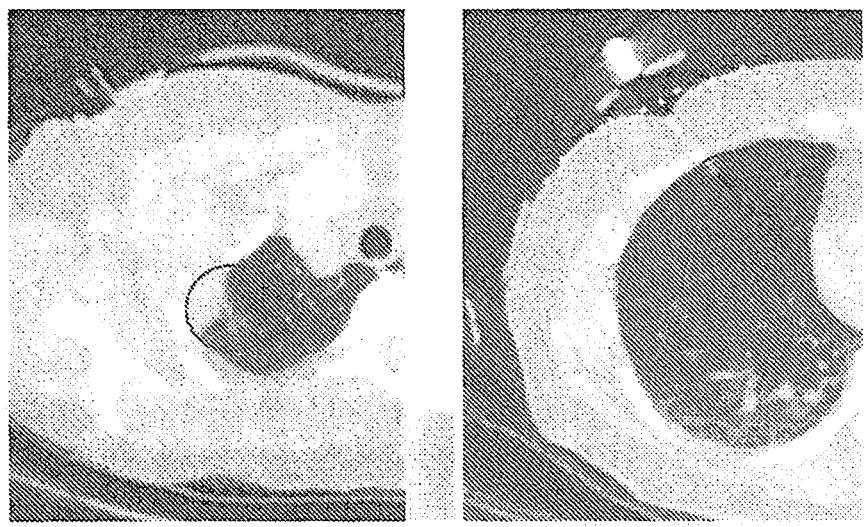
FIG. 22 is a comparison diagram of puncture effect in CT reexamination in Application Example 6 of the invention.

The patient laid herself flat on a CT bed, wherein the thoracic cage was fully exposed, an assistant depicted the positions of suprasternal fossa, sternal angle, anterior median line and xiphoid of the patient by a marking pen. The medical auxiliary apparatus was taken out from an aseptic bag, and it was fixed on the body of the patient by elastic straps. The thoracic surgeon checked that alignment of each locating point was good, without abnormal stress on each side of the apparatus, so the medical auxiliary apparatus could tightly attached the thoracic cage of the affected side of the patient. The thoracic surgeon confirmed patient information, and determined the depth for inserting needle; a thoracic surgeon used sterile gloves to take a puncture needle out; after the patient was required to take a deep breath, the puncture needle was inserted in a predetermined depth for inserting needle in accordance with the preformed hole on the guide rail for inserting needle; so a locating hook was released, the puncture needle was pulled out, disinfecting and packaging routinely; CT reexamination showed that the lesion was hit. No complications were found after half an hour observation, so the patient was moved back to a sickroom, waiting for a surgery, as shown in FIG. 22, CT reexamination confirmed that the path for inserting needle was accurate and the process of puncture was successful.

Application Example 7

Clinical Application of the Method for Locating and Treating a Pulmonary Target Lesion In Vitro According to Example 7

Figure 23:
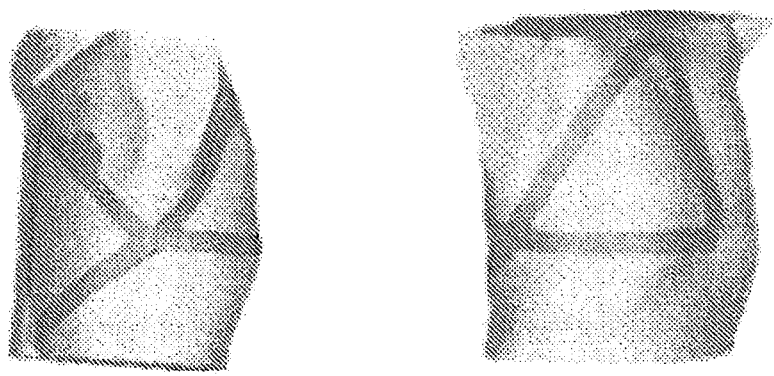
FIG. 23 is a diagram of a butterfly extracorporeal medical auxiliary apparatus for localization/biopsy of a pulmonary target lesion and a digital model of a body surface morphology and an anatomical bony structure in Application Example 7 of the invention.

A male patient, aged 59, was physically examined, a ground-glass nodule was found in a position of right lung through chest CT, a puncture localization was proposed; as shown in FIG. 23, CT before surgery of the patient was utilized to reconstruct a digital model of the chest. After measurement and design, the projection of the pulmonary nodule on the body surface was found between the sixth rib and the seventh rib of the right close to infrascapular line, it was scheduled to insert a needle from dorsal side. 3Dmax was used for building a digital model of the structure, wherein multiple sides, of the butterfly-shaped structure (twin wings) for localization/biopsy were attached to the thoracic wall of the patient, with a width of 3 cm and a thickness of 0.3 cm; wherein one side along the sternum depleted depressions for locating and hollow lines respectively corresponding to suprasternal fossa, sternal angle, anterior median line and xiphoid according to anatomical structure; the other sides were placed along the body surface morphology of the thoracic cage of the patient, the angle locating auxiliary unit was attached to one side which was placed at the back on a relatively high positron. A puncture point of a lesion on a body surface was taken as the point for inserting needle, a connecting line between them was taken as an entry path for inserting needle, a distance from the lesion center to a superior border of the guide rail for inserting needle was taken as the depth for inserting needle, the entry path for inserting needle and the guide rail receiving column were designed; after all design completed, a 3D digital model file was generated and the generated 3D digital model was imported into a printer driver, raw material was assigned to be Nylon powder through layering analysis and internal structure calculation, a final product which was the structure model for localization/biopsy was printed by hot melt layer depositing; then the printed medical auxiliary apparatus for localization/biopsy was sent to a supply room of a hospital for ethylene oxide sterilizing and packaging in an aseptic bag for use, wherein the guide rail for inserting needle could be sterilized under high temperature and high pressure and packaged in an aseptic bag for use.

The patient laid herself flat on a CT bed, wherein the thoracic cage was fully exposed, an assistant depicted the positions of suprasternal fossa, sternal angle, anterior median line and xiphoid of the patient by a marking pen. The medical auxiliary apparatus was taker, out from an aseptic bag, and it was fixed on the body of the pattern by elastic straps. The thoracic surgeon checked that alignment of each locating point was good, without abnormal stress on each side of the apparatus, so the medical auxiliary apparatus could tightly attached the thoracic cage of the affected side of the patient The thoracic surgeon confirmed patient information, and determined the depth for inserting needle; a thoracic surgeon used sterile gloves to take a puncture needle out; after the patient was required to take a deep breath, the puncture needle was inserted in a predetermined depth for inserting needle in accordance with the preformed hole on the guide rail for inserting needle; after repeated aspiration, a few tissues were extracted for sending to pathology department for medical examination; the puncture needle was pulled out, disinfecting and packaging routinely; no complications were found after half an hour observation, so the patient was moved back to a sickroom, wailing for a surgery; pathologic analysis of the needle biopsy indicated a pulmonary adenocarcinoma, which was consistent with the pathological result of intraoperative frozen section examination.

While the above description contains many embodiments, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

The invention claimed is:

1. A method for precise localization and treatment of a target site, wherein the method comprises the following steps:
   S1: a computer-aided design software is used for building a digital model of an anatomical structure of a patient in accordance with tomographic image data of the patient, and a 3D position of the target site is determined based on the digital model of the anatomical structure;
   S2: the computer-aided design software is reused to design a template model for locating a target site which closely fits a body surface or an organ surface of the digital model of the anatomical structure of the patient based on the digital model of the anatomical structure obtained in S1; subsequently, an angle locating auxiliary unit model is designed on the template model for locating the target site according to the 3D position of the target site determined in S1, wherein the angle locating auxiliary unit model comprises an auxiliary tunnel, a relative angle of which is jointly determined by a position of the target site, the position of the angle locating auxiliary unit model and the position of relevant important organ or tissue;
   S3: the template model for locating the target site with the angle locating auxiliary unit model is printed by 3D printing technology, so as to produce the target site locating structure; and
   S4: the target site locating structure produced in S3 is mounted on a corresponding position of a body surface or an organ surface of the patient, then a treatment device is used to correspondingly treat the target site with an assistance of the angle locating auxiliary unit model;
   wherein a method for designing the template model for locating the target site in S2 comprises:
   a. a localization path which passes through the target site and has a shortest distance from the body surface or the organ surface is designed on the digital model of the anatomical structure; a point on the body surface or the organ surface is set as a puncture point according to the localization path; taking a body surface mark or an organ surface mark of the patient as a reference point, an anatomical orientation point is designed on the digital model of the anatomical structure for assisting the target site locating structure in properly placing and locating; and
   b. in accordance with the anatomical orientation point, the localization path and the puncture point, the computer-aided design software is used to design the template model for locating the target site which closely fits the body surface or the organ surface of the digital model of the anatomical structure.

2. The method for precise localization and treatment of the target site as claimed in claim 1, wherein the auxiliary tunnel of the angle locating auxiliary unit model in S2 is configured in the localization path between the target site and the puncture point, wherein the localization path having the shortest distance is configured for detouring around important blood vessels, nerves and bones in the digital model of the anatomical structure.

3. The method for precise localization and treatment of the target site as claimed in claim 1, wherein an auxiliary mechanism for matching a locating of the treatment device is configured on the angle locating auxiliary unit model in S2.

4. The method for precise localization and treatment of the target site as claimed in claim 3, wherein the auxiliary mechanism comprises a fixed frame, a sterilizing hole and a guide rail steel core.

5. The method for precise localization and treatment of the target site as claimed in claim 1, wherein the digital model of the anatomical structure comprises digital models of head and neck, trunk, upper limb and/or lower limb having the target site.

6. The method for precise localization and treatment of the target site as claimed in claim 1, wherein localization, size, depth and number of the target site are labeled and calculated on the digital model of the anatomical structure based on tomographic image data of the patient in S1.

7. The method for precise localization and treatment of the target site as claimed in claim 1, wherein the treatment device is selected from a group consisting of a biopsy gun, a locating needle, a radiation source, an electrode patch and a blood lancet in S4.

8. A method for precise localization and treatment of a target site in vitro, wherein the method comprises the following steps:
   S1: a computer-aided design software is used for building a digital model of a body surface morphology and an anatomical bony structure of a patient in accordance with tomographic image data of the patient, and a 3D position of the target site is determined based on the digital model of the body surface morphology and the anatomical bony structure;
   S2: the computer-aided design software is reused to design a template model for locating an extracorporeal target site which closely fits a body surface of the digital model of the body surface morphology and the anatomical bony structure of the patient based on the digital model of the body surface morphology and the anatomical bony structure obtained in S1; subsequently, an angle locating auxiliary unit model is designed on the template model for locating the extracorporeal target site according to the 3D position of the target site determined in S1, wherein the angle locating auxiliary unit model comprises an auxiliary tunnel, a relative angle of which is jointly determined by a position of the target site, the position of the angle locating auxiliary unit model and the position of relevant important organ or tissue;
   S3: the template model for locating an extracorporeal target site with the angle locating auxiliary unit model is printed by 3D printing technology, so as to produce an extracorporeal target site locating structure having an auxiliary tunnel; and
   S4: the extracorporeal target site locating structure produced in S3 is mounted on a corresponding position of a body surface of the patient, then a treatment device is used to correspondingly treat the target site through a micro incision during surgery with an assistance of the angle locating auxiliary unit model;
   wherein a method for designing the template model for locating the extracorporeal target site in S2 comprises:
   a. a localization path which passes through the target site and has a shortest distance from the body surface is designed on the digital model of the body surface morphology and the anatomical bony structure; a point on the body surface is set as a puncture point according to the localization path; taking a body surface mark of the patient as a reference point, an anatomical orientation point is designed on the digital model of the body surface morphology and the anatomical bony structure for assisting the extracorporeal target site locating structure in properly placing and locating; and b. in accordance with the anatomical orientation point, the localization path and the puncture point, the computer-aided design software is used to design the template model for locating the extracorporeal target site which closely fits the body surface of the digital model of the body surface morphology and the anatomical bony structure.

9. The method for precise localization and treatment of the target site in vitro as claimed in claim 8, wherein the auxiliary tunnel of the angle locating auxiliary unit model in S2 is configured in the localization path between the target site and the puncture point, wherein the localization path having the shortest distance is configured for detouring around important blood vessels, nerves and bones in the digital model of body surface morphology and the anatomical bony structure.

10. The method for precise localization and treatment of the target site in vitro as claimed in claim 8, wherein the anatomical orientation point corresponds to the body surface mark of the patient, which is selected from at least two of a group consisting of thorax surface, suprasternal fossa, sternoclavicular joint, sternal angle, mesosternum, xiphoid, anterior median line, posterior median line and spinous process.

11. The method for precise localization and treatment of the target site in vitro as claimed in claim 10, wherein a fixing structure for closely fitting the body surface mark is configured on an internal surface of the extracorporeal target site locating structure.

12. The method for precise localization and treatment of the target site in vitro as claimed in claim 11, wherein the fixing structure is selected from at least one of a group consisting of projection structure, depression structure, linear hollow structure and circular hollow structure.

13. The method for precise localization and treatment of the target site in vitro as claimed in claim 8, wherein the treatment device is selected from a group consisting of a biopsy gun, a locating needle, a radiation source, an electrode patch and a blood lancet in S4.

\* \* \* \* \*